(12) United States Patent
Zarandi et al.

(10) Patent No.: US 10,653,346 B2
(45) Date of Patent: May 19, 2020

(54) HAND-HELD OPTICAL SCANNER FOR REAL-TIME IMAGING OF BODY COMPOSITION AND METABOLISM

(71) Applicant: The Regents of the University of California, Oakland, CA (US)

(72) Inventors: Soroush Mohammad Mirzaei Zarandi, La Habra, CA (US); Bruce J. Tromberg, Irvine, CA (US); Thomas D. O'Sullivan, Laguna Hills, CA (US); Siavash Sedighzadeh Yazdi, Irvine, CA (US); Albert Cerussi, Cupertino, CA (US)

(73) Assignee: The Regents of the University of California, Oakland, CA (US)

( * ) Notice: Subject to any disclaimer, the term of this patent is extended or adjusted under 35 U.S.C. 154(b) by 573 days.

(21) Appl. No.: 15/416,942

(22) Filed: Jan. 26, 2017

(65) Prior Publication Data
US 2017/0209083 A1    Jul. 27, 2017

Related U.S. Application Data

(60) Provisional application No. 62/287,803, filed on Jan. 27, 2016.

(51) Int. Cl.
| *A61B 5/1455* | (2006.01) |
| *A61B 5/145* | (2006.01) |
| *A61B 5/024* | (2006.01) |
| *A61B 5/08* | (2006.01) |
| *A61B 5/00* | (2006.01) |

(52) U.S. Cl.
CPC ...... *A61B 5/14551* (2013.01); *A61B 5/02416* (2013.01); *A61B 5/0816* (2013.01); *A61B 5/14546* (2013.01); *A61B 5/7278* (2013.01)

(58) Field of Classification Search
CPC . A61B 5/14551; A61B 5/7278; A61B 5/0816; A61B 5/14546; A61B 5/02416
See application file for complete search history.

(56) References Cited

U.S. PATENT DOCUMENTS

| 2007/0219450 A1* | 9/2007 | Azar | A61B 5/0091 600/476 |
| 2011/0190613 A1* | 8/2011 | Zhang | A61B 5/1455 600/328 |

* cited by examiner

*Primary Examiner* — Eric F Winakur
*Assistant Examiner* — Abid A Mustansir
(74) *Attorney, Agent, or Firm* — Marcus C. Dawes; Daniel L. Dawes

(57) ABSTRACT

A low cost portable high speed quantitative system for diffuse optical spectroscopic imaging of human tissue. The hybrid system (CWFD) can measure absolute optical properties from 660 nm to 980 nm and recover all tissue chromophore concentrations. The standalone FD module can be utilized to measure scattering at every measurement and recover deoxygenated and oxygenated hemoglobin concentrations. The CW module can operate concurrently with the FD module to also measure water and lipid. The high temporal resolution and large signal-to-noise ratio of the CWFD system may be used to explore tissue oximetry, vascular occlusion, and paced breathing models to measure and analyze tissue hemodynamics response to changes in blood flow. Continuous monitoring of vasculature response to various modified blood perfusion conditions can provide information about local tissue metabolism and physiological state (dysfunction).

19 Claims, 18 Drawing Sheets
(5 of 18 Drawing Sheet(s) Filed in Color)

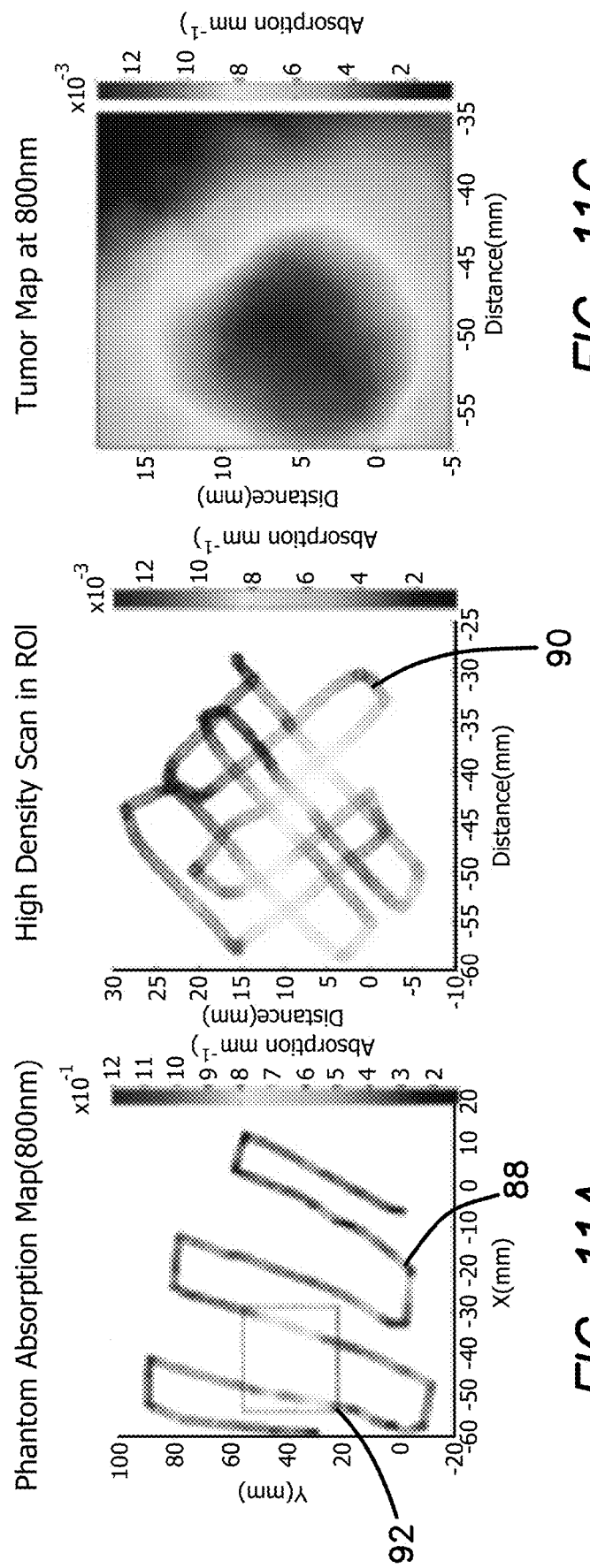

HAND-HELD OPTICAL SCANNER FOR REAL-TIME IMAGING OF BODY COMPOSITION AND METABOLISM

GOVERNMENT SUPPORT

This invention was made with government support under P41EB015890, R01CA142989, funded by National Institute of Health (NIH). The government has certain rights in the invention.

RELATED APPLICATIONS

This application is related to provisional patent application, entitled, A HAND-HELD OPTICAL SCANNER FOR REAL-TIME IMAGING OF BODY COMPOSITION AND METABOLISM, Ser. No. 62/287,803, filed on Jan. 27, 2016, under 35 USC 119, which is incorporated herein by reference.

BACKGROUND

Field of the Technology

The invention relates to the field of medical devices and methods, namely an optical instrument and a computational model for scanning and imaging of human body composition including tissue water, lipid, oxygenated hemoglobin and deoxygenated hemoglobin content.

Description of the Prior Art

Diffuse optical spectroscopic imaging (DOSI) methods provide a low-cost, non-invasive approach for obtaining critical information regarding the structure and function of tissue. They use Near Infrared (NIR) light between 650 and 1000 nm to interrogate tissue to depths of several centimeters beneath the surface including the brain, breast, bone, abdomen and muscle. Also, the low energy output and non-ionizing radiation of the NIR spectrum causes no damage to the tissue, making DOSI a viable method for medical imaging purposes. Access to important physiological processes in the human body requires penetrating through 2-3 cm of tissue. DOSI provides information about tissue function and structure through the detection of four major components found in tissue: oxygenated hemoglobin, deoxygenated hemoglobin, water, and lipids Tissue acts as a highly scattering turbid medium with low absorption when interacting with NIR light. As photons enter the tissue, they undergo multiple scattering and absorption events that cause the photons to diffuse in random directions. Diffusion models have been developed for light-tissue interactions to study subsurface tissue characteristics. Three main modalities currently exist for measuring tissue optical properties: continuous wave (CW), frequency domain (FD), and time domain (TD) imaging. The CW (time-unresolved) method provides qualitative information by measuring only relative changes in tissue components. This technique provides fast measurements and simple circuit designs, but is unable to separate scattering from absorption in a single measurement. Moreover, these techniques assume constant scattering and neglect possible changes in scattering occurring during a continuous measurement. This assumption can introduce significant errors when accurately calculating absorber concentrations in the tissue.

In contrast, TD and FD methods (time-resolved) provide quantitative approaches to optical imaging by separating absorption from scattering. A TD technology implements a short pulse beam (<100 ps) into tissue that broadens as it reaches the detector due to the scattering and absorbing events within the tissue. Despite its ability to obtain both scattering and absorption information, time domain imaging has a few limitations that prevent the translation of this technology to a portable real-time clinical friendly system. TD's optoelectronic high cost and complex circuitry reduces spectral bandwidth; thereby in applications such as breast cancer, information about water and fat content are inaccessible.

The FD modality implements the Fourier transform of the TD approach. On the source side, the FD system modulates the light source intensity with a Radio Frequency (RF) signal as the light enters the tissue. On the detector side, the AC amplitude, DC average intensity, and phase shift are measured using photon detectors. These amplitude and phase measurements are made at multiple frequencies and are subsequently fed into a frequency-domain diffusive analytical model of light propagation for a (semi)infinite medium to extract optical properties (absorption and scattering). FD also has limited spectral bandwidth similar to TD modality. However, FD circuit complexity, cost, and size are improved in comparison to TD. Because a limited number of wavelengths can affect the recovering of chromophore concentrations significantly, a large wavelength range is required. Achieving this goal, covering a large spectral bandwidth, using time-resolved techniques requires tunable sources or a large collection of laser diodes resulting in a bulky slow expensive system with complex maintenance requires tunable sources or a large collection of laser diodes resulting in a bulky slow expensive system with complex maintenance.

One strategy for overcoming both time-resolved and time-unresolved technique limitations is development of a hybrid method that utilizes both modalities in tandem to extract near-infrared absorber concentrations accurately. Our group has developed a combined broadband quantitative platform to recover absolute NIR absorption and scattering spectra of biological tissues. The quantitative information is provided by the Frequency Domain Photon Migration (FDPM) module while large spectral bandwidth from 650 nm to 998 nm with step of 0.5 nm (697 wavelengths in total) is provided by the steady state module. Four tissue chromophore concentrations are extracted from broadband spectra. Although this platform is powerful and has rich information content, however it has a few limitations such as speed, cost and size. Depending on media attenuation and required source-detector spacing, a single tissue measurement with this system can take up to 5 seconds.

What is needed is an apparatus and method for expanding spectral bandwidth and improving acquisition speed in diffuse optical spectroscopic imaging which also improves system costs and dimensions in order to lower barriers to clinical access. The apparatus and method should also be an inexpensive integrated method for continuous spectroscopic imaging in human tissues.

BRIEF SUMMARY

The current device is capable of providing rapid information about tissue structure and composition by measuring four major biochemical components found in tissue: oxygenated hemoglobin, deoxygenated hemoglobin, water, and lipids. These measurements can be combined to form quantitative indices of tissue oxygen saturation and tissue hydration. We have developed and built a low cost, portable multi-wavelength continuous wave (CW) system for real-time optical imaging of human tissue function and composition. This system measures four tissue chromophore concentrations (water, lipid, deoxygenated hemoglobin, and oxygenated hemoglobin) and indices of tissue oxygen saturation and tissue hydration, using at least four near-infrared wavelengths ranging from 600 nm to 1000 nm. These tissue components and indices can be measured using a hand-held scanning probe over scalable regions of interest in "real time" by using dedicated computational methods for image rendering and visualization. In addition, the data can be further processed to reveal dynamic fluctuations in these parameters that occur with a variety of events and perturbations, including (but not limited to) the beating of the heart, respiration, blood pressure, etc. as well as the impact of drugs, radiation, and other modulators on tissue. The device uses frequency multiplexing to achieve sampling rates up to 250 Hz. This system is immune to background noise from ambient light by utilizing low-frequency modulation and bandpass filtering. A dedicated algorithm is used to account for tissue-type dependent optical path length changes and calculate tissue biochemical constituents without any other prior assumptions.

The performance of this system and its equivalency to previous diffuse optical spectroscopy systems has been tested and validated both tissue phantoms and in-vivo in various tissues. The system enables either continuous scanning of the body or the placement of the probe in discrete locations. We have demonstrated in-vivo applications of this instrument by measuring abdomen, muscle and brain tissues. The extremely fast data acquisition enables high-resolution characterization of the physiological pulsatile waveforms. The modularity of the device allows for expansion of optical wavelengths and the integration and co-registration with other methods, including, but not limited to, frequency-domain (FD) and time domain (TD) methods, broadband spectroscopy, motion sensing and tracking devices, and other radiologic imaging devices including, but not limited to, ultrasound, MRI, x-ray, EEG, and nuclear imaging methods.

The illustrated embodiments of the invention include an apparatus for combining continuous wave and Fourier domain diffuse optical spectroscopic imaging (CWFD DOSI). The apparatus includes: a Fourier domain pulse modulated (FDPM) module; a continuous wave diffuse optical spectroscopic (CW) module; and a computerized controller coupled to the FDPM and CW module to control the FDPM module and CW module in a multimode operation.

The controller in a first mode activates or controls only the FDPM module to make data measurements to provide quantitative data by decoupling scattering from absorption at a plurality of wavelengths sensitive to deoxygenated and oxygenated hemoglobin.

The controller in a second mode activates or controls the CW module at a plurality of data acquisition rates and plurality of wavelengths.

The controller in a third mode operates the FDPM module once to establish a baseline to measure scattering coefficients for use for later data correction processing and operates the CW module to make all remaining measurements.

The controller in a fourth mode operates the FDPM module and CW module in an interleaved sequence to take consecutive measurements to measure scattering coefficients for use in later data correction processing in each subsequent measurement.

The apparatus further includes a computer coupled to the controller for processing data measured by the FDPM module and CW module, where the computer calculates quantitative information relating to water, deoxy-Hb, oxy-Hb and lipid in tissue from the data.

The apparatus further includes a probe through which data is obtained by the FDPM module and CW module and a tracking subsystem coupled to the controller to continuously measure linear displacement of the probe and rotational displacement of the probe.

The FDPM module and/or CW module include laser sources with wavelengths selected below and above an isosbestic point where both deoxygenated hemoglobin and oxygenated hemoglobin have the same absorption coefficients, so that tissue oximetry is performed.

The apparatus further includes a probe coupled to the FDPM and CW module for data acquisition and where the probe is applied to thick tissue to measure tissue oxygenation, heart rate, or respiration rate.

The apparatus further includes a probe coupled to the FDPM and CW module for data acquisition and where the probe is applied to thick tissue to measure tissue oxygenation, heart rate, respiration rate, or dynamic vascular oxygenation response due to vascular occlusion.

The illustrated embodiments of the invention also extend to a method for combining continuous wave and Fourier domain diffuse optical spectroscopic imaging (CWFD DOSI). The method includes the steps of: applying an optical probe to thick tissue of a subject; selectively operating a Fourier domain pulse modulated (FDPM) module coupled to the probe and a continuous wave diffuse optical spectroscopic (CW) module coupled to the probe in a multimode operation, the FDPM and CW modules being operated in combination under control of a computerized controller coupled to the FDPM and CW modules; continuously tracking a two dimensional position of the probe; and data processing optical scattering and absorption data acquired by the FDPM and CW modules correlated to the continuous tracking of the probe to derive a two dimensional map of a plurality of chromophore concentrations in thick tissue.

The step of selectively operating a Fourier domain pulse modulated (FDPM) module coupled to the probe and a continuous wave diffuse optical spectroscopic (CW) module coupled to the probe in a multimode operation includes a first mode for controlling the FDPM module to make data measurements to provide quantitative data by decoupling scattering from absorption at a plurality of wavelengths sensitive to deoxygenated and oxygenated hemoglobin.

The step of selectively operating a Fourier domain pulse modulated (FDPM) module coupled to the probe and a continuous wave diffuse optical spectroscopic (CW) module coupled to the probe in a multimode operation includes a second mode for controlling the CW module at a plurality of data acquisition rates and plurality of wavelengths.

The step of selectively operating a Fourier domain pulse modulated (FDPM) module coupled to the probe and a continuous wave diffuse optical spectroscopic (CW) module coupled to the probe in a multimode operation includes a third mode for operating the FDPM module once to establish a baseline to measure scattering coefficients for use for later data correction processing and operating the CW module to make all remaining measurements.

The step of selectively operating a Fourier domain pulse modulated (FDPM) module coupled to the probe and a continuous wave diffuse optical spectroscopic (CW) module coupled to the probe in a multimode operation includes a fourth mode for operating the FDPM module and CW module in an interleaved sequence to take consecutive measurements to measure scattering coefficients for use in later data correction processing in each subsequent measurement.

The step of data processing optical scattering and absorption data acquired by the FDPM and CW modules correlated to the continuous tracking of the probe to derive a two dimensional map of a plurality of chromophore concentrations in thick tissue includes the step of calculating quantitative information relating to water, deoxy-Hb, oxy-Hb and lipid in tissue from data acquired by the FDPM and CW modules.

The step of continuously tracking a two dimensional position of the probe includes the step of continuously measuring linear displacement of the probe and rotational displacement of the probe.

The illustrated embodiments of the invention include a method for combining continuous wave and Fourier domain diffuse optical spectroscopic imaging (CWFD DOSI). The includes the steps of: applying an optical probe to thick tissue of a subject; selectively operating a Fourier domain pulse modulated (FDPM) module coupled to the probe and a continuous wave diffuse optical spectroscopic (CW) module coupled to the probe in a multimode operation, the FDPM and CW modules being operated in combination under control of a computerized controller coupled to the FDPM and CW modules; and data processing optical scattering and absorption data acquired by the FDPM and CW modules, where the FDPM module and/or CW module include laser sources with wavelengths selected below and above an isosbestic point where both deoxygenated hemoglobin and oxygenated hemoglobin have the same absorption coefficients, so that tissue oximetry is performed.

The step of data processing to perform tissue oximetry further includes the step of measuring tissue oxygenation, heart rate, respiration rate, or dynamic vascular oxygenation response due to vascular occlusion.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7b is a perspective view of the phantom of FIG. 7a.

FIG. 11a is a color coded absorption map using a continuous scanning pattern over a region of interest in a phantom using CWFD. FIG. 11b is an absorption color coded absorption map using a high density continuous scanning pattern over a region of interest using CWFD. FIG. 11c is a color coded absorption map in enlarged scale of the region of interest scanned in FIGS. 11a and 11b using CWFD.

FIG. 12a is a grid scanning patterned, color coded absorption map using SSFD created from the same phantom used in FIGS. 11a-11c. FIG. 12b is a color coded absorption map interpolated from the SSFD scan of FIG. 12a. FIG. 12c is a color coded absorption map in enlarged scale of the region of interest scanned in FIG. 12a using SSFD.

FIG. 15c is a time graph of the oxy-Hb in μM of the data of FIG. 15a.

Figure 1:
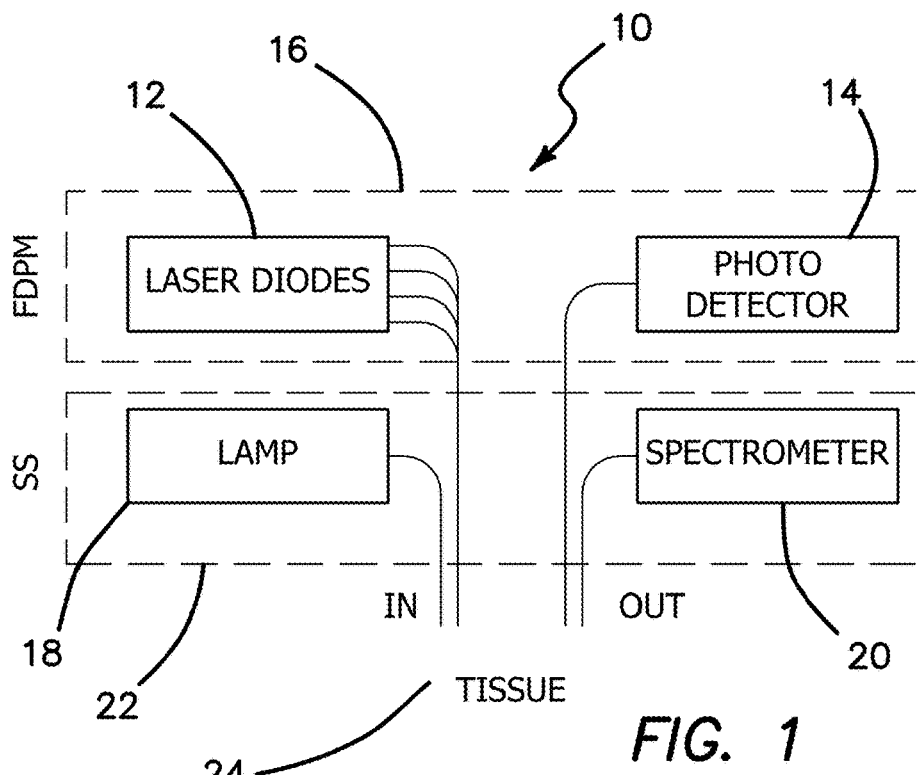
FIG. 1 is a block diagram of the prior art Fourier domain pulsed modulated (FDPM) and steady state (SS) DOSI system. Although similar at the high-level abstraction of the block diagram of FIG. 1, the FDPM module of the illustrated embodiments of the invention may differ from that in the prior art according to the detailed description below.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Diffuse optical spectroscopic imaging (DOSI) provides a low-cost, non-invasive method for obtaining critical information regarding the architecture and function of tissue. Access to important physiological processes in the human body requires penetrating through 2-3 cm deep in tissue. DOSI technology uses Near Infrared (NIR) light between 650 and 1000 nm to interrogate tissue. NIR light has a high penetration depth of several centimeters through tissues including the brain, breast, and muscle as a result of the tissue's relatively small absorption rate. Also, the low energy output and non-ionizing radiation of the NIR spectrum causes no damage to tissue, making DOSI a viable method for medical imaging purposes. DOSI provides information about tissue function and structure through the detection of four major components found in tissue: oxygenated hemoglobin, deoxygenated hemoglobin, water, and lipids.

Tissue acts as a highly scattering turbid medium with low absorption when interacting with light. As photons enter the tissue, they undergo multiple scattering and absorption events that cause the photons to diffuse in random directions. Diffusion models have been developed for light-tissue interactions to study subsurface tissue characteristics. Three main modalities currently exist for measuring tissue optical properties: continuous wave (CW), frequency domain (FD), and time domain (TD) imaging.

The CW (time-unresolved) method provides qualitative information by measuring only relative changes in tissue components. This technique provides fast measurements and simple circuit designs, but is unable to separate scattering from absorption in a single measurement. Moreover, constant wave measuring techniques assume constant scattering and neglect possible changes in scattering occurring during a continuous measurement. This assumption can introduce significant errors when accurately calculating absorber concentrations in the tissue.

In contrast, TD and FD methods (time-resolved) provide quantitative approaches to optical imaging by separating absorption from scattering. A TD technology implements a short pulse beam (<100 ps) into tissue that broadens as it reaches the detector due to the scattering and absorbing events within the tissue. Despite its ability to obtain both scattering and absorption information, time domain imaging has a few limitations that prevent the translation of this technology to a portable real-time, clinical friendly system. TD's optoelectronic high cost and complex circuitry reduces spectral bandwidth; thereby in applications such as breast cancer, information about water and fat content are inaccessible.

Similar to time domain imaging, the FD modality implements the Fourier transform of the TD approach. On the source side, the FD system modulates the light source intensity with a radio frequency (RF) signal as the light enters the tissue. On the detector side, the AC amplitude, DC average intensity, and phase shift are measured using photon detectors. These amplitude and phase measurements are made at multiple frequencies and are subsequently fed into a frequency-domain diffusive analytical model of light propagation for a (semi)infinite medium to extract optical properties (absorption and scattering). FD also has limited spectral bandwidth similar to TD modality. However, FD circuit complexity, cost, and size are improved in comparison to TD. Because a limited number of wavelengths can affect the recovering of chromophore concentrations significantly, a large wavelength range is required. However, achieving this goal, covering a large spectral bandwidth, using time-resolved techniques requires tunable sources or a large collection of laser diodes resulting in a bulky, slow and expensive system with complex maintenance.

Figure 3:
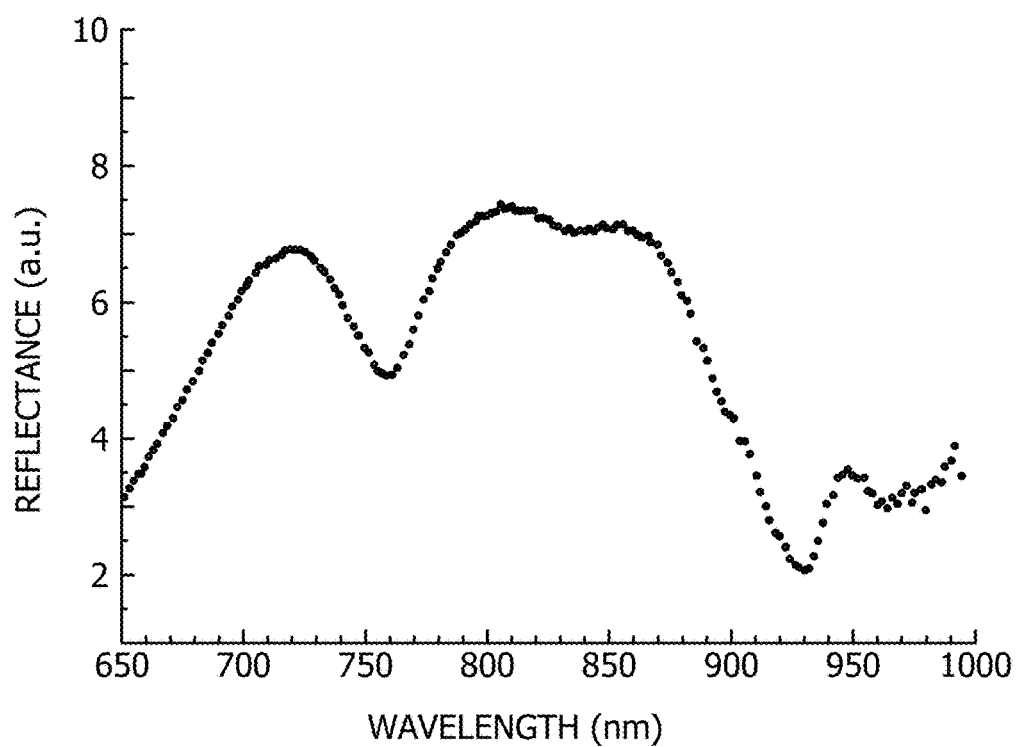
FIG. 3 is a graph of the scattered corrected CW broadband reflectance as a function of wavelength as measured by the apparatus of FIG. 1.
Figure 4:
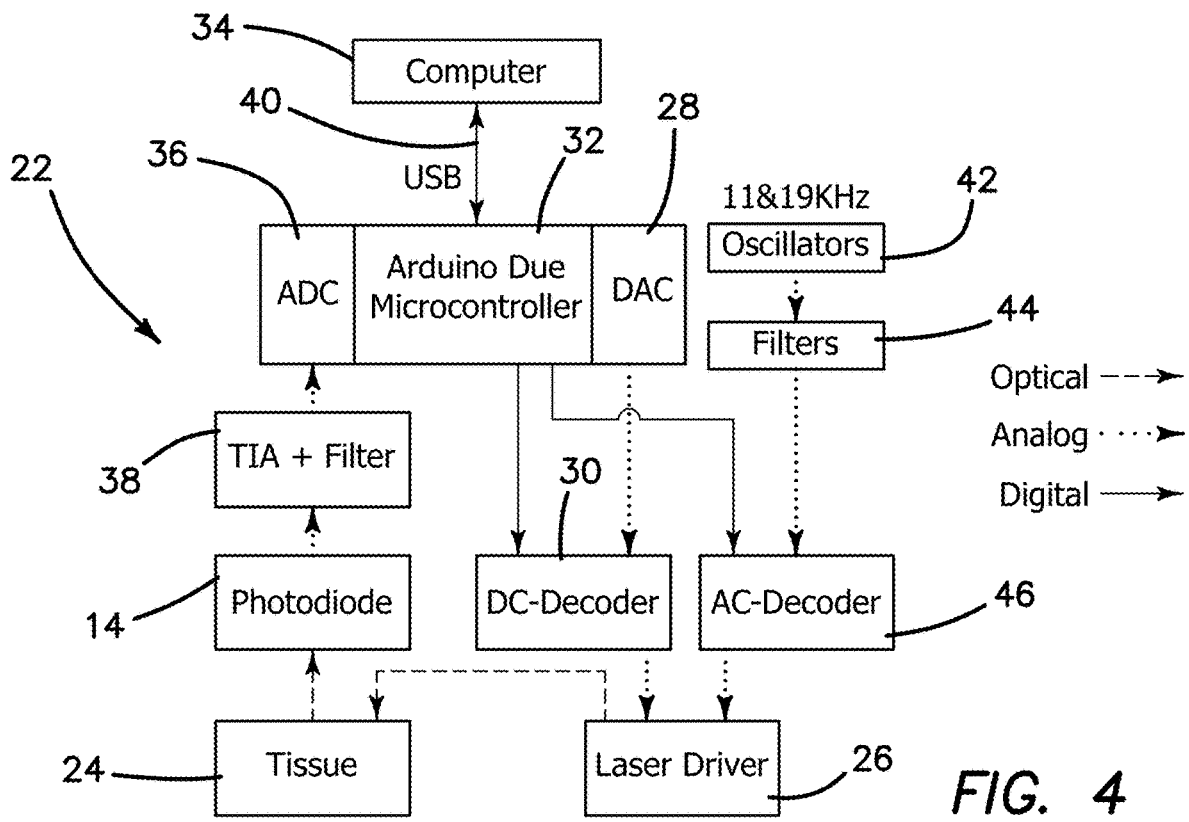
FIG. 4 is a block diagram of the CW module of the illustrated embodiment of the invention which is an improvement over the apparatus of FIG. 1.

The illustrated embodiment of the invention is a hybrid DOSI platform that utilizes FD and CW techniques in tandem to extract near-infrared absorber concentrations accurately as diagrammatically shown in FIG. 4. The conventional apparatus 10 of FIG. 1 includes a plurality of laser diodes 12 and a photodetector 14 in a Fourier domain pulsed modulated (FDPM) module 16. A steady state or CW module 22 includes a CW laser bank 18 and a spectrometer 20. Tissue 24 is sampled or measured by apparatus 10 simultaneously with the FD and CW modality probes. The FDPM module 16 provides quantitative information by decoupling scattering from absorption at several wavelengths as shown in FIGS. 2a and 2b. Scattering broadband spectrum is obtained by fitting FD scattering data into a power curve as shown in FIG. 2b. The CW broadband reflectance measurement shown in FIG. 3 will be corrected by using a scattering spectrum. Then, the tissue NIR absorption spectrum is calculated from the scatter-corrected reflectance measurement resulting in FIG. 2b. In the last step, absolute tissue chromophore concentrations is extracted from a broadband quantitative absorption spectrum. The FDPM and CW modules are coupled to and controlled by control circuitry described below.

Although this combined technology takes advantage of both FD and CW modalities to provide quantitative broadband scattering and absorption spectra, there is still a need for optimization of platform speed, cost and size. For instance, broadband light sources and spectrometers used in this technology for increasing spectral bandwidth causes slow data acquisitions and significant increases in the overall cost.

Figure 2A:
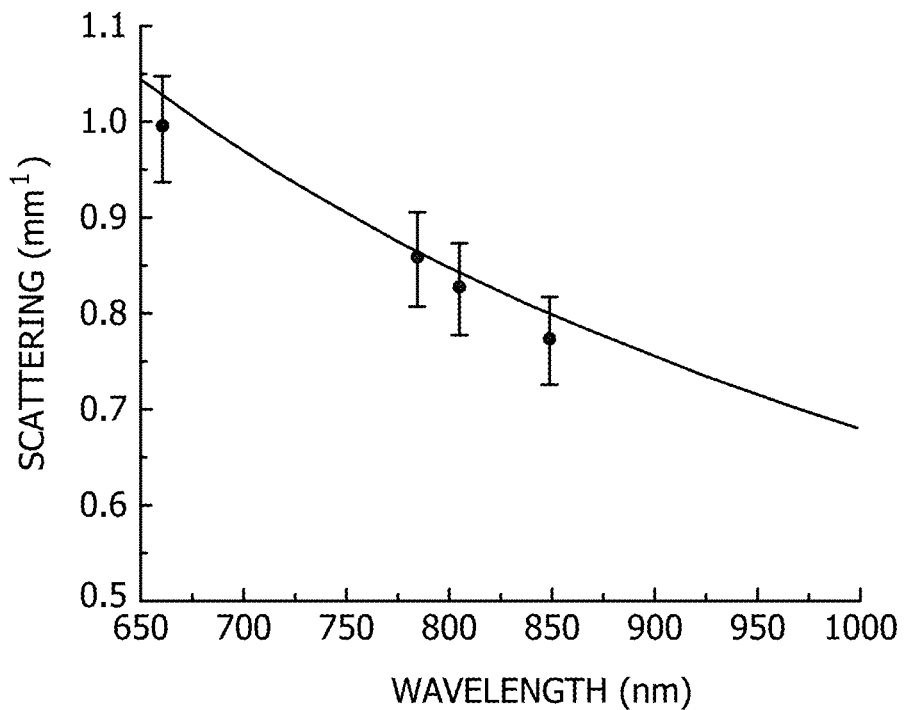
FIG. 2a is a graph of the scattering measured from a tissue sample as a function of wavelength provided by the FDPM module of FIG. 1.
Figure 2B:
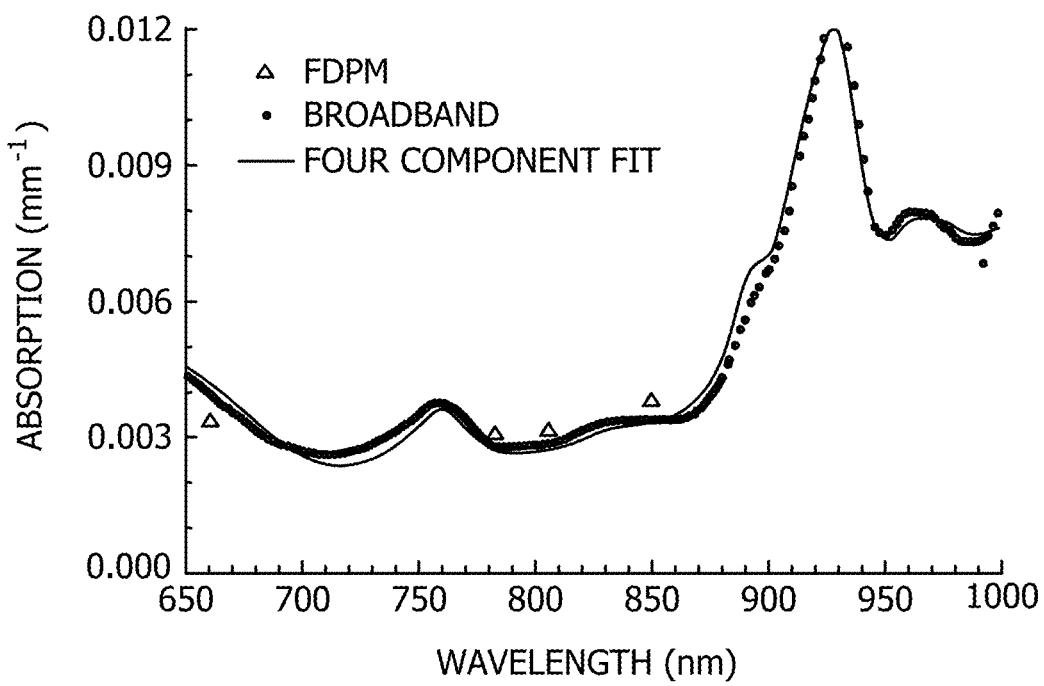
FIG. 2b is a graph of the absorption measured from a tissue sample as a function of wavelength provided by the FDPM module of FIG. 1.

For real-time optical scanning and creating functional maps of biological tissues, conventional DOSI technology of FIG. 1 requires improvement in two areas. First, for increasing the measurement rates, the broadband light source and the spectrometer combination need to be replaced with a module capable of fast data acquisition. However, the overall system's large spectral bandwidth and consequently its ability to recover water-lipid data should be maintained. Development of a DOSI technology capable of imaging at high rates with rich spectral content is a technical challenge. Removal of broadband source-detector platform requires addition of a reasonable number of sources which results in slower data acquisition. Therefore, the improved platform should be capable of sub-second illumination and detection of several wavelengths at a single location. Second, to take advantage of real-time optical scanning, integration of a tracking system into the optical probe is required to record the measurement paths on tissue surface. Co-registration of rapid optical measurements with tracking sensors data would provide high density tissue chromophore maps.

A large spectral bandwidth for recovering the water and lipid data content can be used to provide functional images of not only breast tissue, but also other tissues such as abdomen and muscle tissues. Adipose tissue plays an important role in the development of metabolic dysfunctions. We have studied a group of volunteers undergoing weight loss using a calorie restriction strategy. We measured their abdomen tissue and reconstruct two dimensional maps of chromophore concentration throughout the weight loss program, allowing us to monitor changes in abdomen tissue structure and function. Similar to breast cancer studies, we took the measurements in a grid pattern every 10 mm and interpolated to create the two dimensional image maps.

We generated maps of all four tissue chromophore concentrations in addition to tissue optical index (TOI). TOI summarizes all tissue components into one single variable and is sensitive to the metabolic activity of tissue.

$$TOI=(DeoxyHB \times Water)/Lipid$$

Besides improving imaging speed, system size, and cost, this improved platform of FIG. 4 also enables us to delve into applications such as real-time monitoring of tissue hemodynamics. Moreover, vital signals such as heart rate and respiration rate can be extracted from thick tissues using this system. These physiological signals' frequencies are in a range from 0.2 Hz to 3 Hz, thereby for accurate data recovery, a multi-wavelength imaging system with minimum 20 Hz data acquisition rate is required. The system of FIG. 1 operates with four wavelengths at 80 Hz in CW mode. We can correct the CW measurements with the scattering coefficients recovered in baseline using FDPM module. This platform enables continuous investigation of pulsatile waveforms in thick tissues as well as characterization of hemodynamics response to stimuli.

Frequency Domain Module

The FDPM module of the illustrated embodiment is consistent with conventional design principles and hence will be only outlined below without limitation as to details which are well known in the art. Hence, with respect only to the FDPM module of the illustrated embodiment of the invention reference will be generally made to FIG. 1. The FDPM module 16 comprises a signal generator coupled to a laser light source and a driver collectively denoted by laser diodes 12 in FIG. 1, and an avalanche photodidode (APD) 14. For signal isolation and SNR improvement, electronic filters and amplifiers (not shown) are used for connection to each component. The laser driver modulation frequency range (50 MHz to 300 MHz) is too large to be generated directly from oscillators, thus instead, a variable frequency in the 2 to 2.94 GHz band is mixed with a fixed 3-GHz frequency. The signal generator of laser diodes 12 includes a conventional phase-rocked loop (PLL) generator generates stable and precise stable frequencies by merging the stability of a 10-MHz temperature compensated crystal oscillator (TCXO) (not shown) with the flexibility of a voltage-controlled oscillator (VCO) (not shown).

Fluctuations in laser power caused by temperature changes are compensated through a feedback loop. An automatic power control (APC) system (not shown) is embedded for each laser by monitoring its photodiode pin. An operational amplifier (op-amp) (not shown) compares voltage induced by the digital potentiometer (not shown) to the voltage induced by the photodiode to adjust laser power precisely. This is an important feature for medical devices since temperature changes in semiconductors are inevitable as a result of long measurement intervals in clinic.

The laser diodes' intensities are modulated from 50 MHz to 300 MHz on the source side sequentially, and changed in amplitude and phase shifted (measured by a custom heterodyne structure not shown) on the detector side. Calibrated amplitude and phase measurements are fitted to diffusion models to extract absorption and scattering optical properties.

Continuous Wave Module

Innovation in the combined CW-FD system lies in the CW module 22. We designed a low cost portable (10 cm×5.5 cm×4.25 cm) CW module 22 for real-time spectroscopic imaging in diffuse media. This system measures four tissue chromophore relative concentrations (water, lipid, deoxygenated and oxygenated hemoglobin) at four near-infrared wavelengths ranging from 660 nm to 980 nm, in real-time. The module 22 operates at various sample rates from 50 Hz to 250 Hz depending on the number of wavelengths needed for illumination (or application). Module 22 expands spectral bandwidth and improves acquisition speed by only measuring changes in the amplitude. The CW module 22 has a 50 dB dynamic range, enabling measurements in tissue 24 with source-detector spacing up to 4 cm; it can also resolve 0.00015 mm$^{-1}$ changes in absorption with the ability to detect a minimum 17 pW. The CW module 22 frequency-encodes wavelengths for parallel illumination resulting in rapid data acquisition. The module 22 suppresses background noise from ambient light by utilizing low-frequency modulation and narrow bandpass filters on the source and detector sides, respectively.

A more detailed block diagram of the current CW module 22 may be seen in FIG. 4. DC bias current for driving a laser driver 26 is provided and regulated through a plurality of analog outputs of digital-to-analog converter (DAC) 28 of a microcontroller 30 (e.g. Arduino Due) through DC decoder 30. Microcontroller 32 in turn is coupled through a USB port to computer 34, which provides overall programmatic control. Lasers 12 are modulated at low frequencies (11 and 19 KHz) through laser driver 26 by oscillators 42 and filters 44 coupled to AC decoder 46, where amplitude data is considered only, and phase shifts introduced by multiple light scattering are negligible. This technique protects the module 22 from background ambient light noise since any signal out of modulation frequency will be rejected both on hardware (detection platform) and software sides. A plurality of narrowband transimpedance amplifiers (TIA) with active filters, collectively denoted by reference numeral 38, are added after a photodiode 14 to detect light from a tissue 24. In order to have a low-cost portable system for clinical usage, and to reduce cost and size, both the source (laser driver 26) and detection (TIA and filter 38) platforms were custom-designed instead of using commercial components. The analog input pins on the microcontroller 32 are coupled to an analog-to-digital converter (ADC) 36. The ADC 36 has 12-bit resolution across 0-3.3V, and it can be configured to operate at 1 MSPS rate. The data are sent to a computer 34 through a serial USB port 40. At the laptop end, waveform data is fed to digital signal processing algorithms to extract FFT power spectra and peaks at corresponding laser modulation frequencies.

Combination of Frequency and Continuous Wave

The illustrated embodiment of the invention also includes a central control program for computer 34 to communicate with both CW and FDPM modules 16 and 22. The algorithm was based on National instruments CVI platform. The computer 34 triggers a FDPM measurement by sending commands over the ethernet to the FDPM microcontroller (not shown). Next, the computer 34 communicates with CW Arduino microcontroller 32 over the serial USB 40 to initiate measurement. The FDPM measurement time can change based on number of modulation frequencies and number of wavelengths. We usually use all four diodes in the FDPM module 16. The CW measurement or data acquisition rate can be set according to the number of wavelengths and number of required measurements. At the minimum, ten CW measurements are required which will take 40 to 125 msec.

There are four modes of operation for the system. In the first mode, the FDPM module 16 is the only one functional. This mode provides quantitative information by decoupling scattering from absorption at four wavelengths sensitive to deoxygenated and oxygenated hemoglobin. In the second mode, which is the fastest method, the CW module 22 operates at different rates and number of wavelengths from 80 Hz (four wavelengths) to 250 Hz (two wavelengths). The third mode, which was not previously available, can operate once with the FDPM module 16 at the baseline to measure scattering coefficients and the rest of the measurements with the CW module 22. In this mode, we can take advantage of FDPM module's 16 ability to provide quantitative information (scattering) and CW module's 22 fast data acquisition. The main assumption in this mixed third mode is that alterations in scattering throughout the measurements relative to the baseline are negligible (less than 5-10%). Basically, the second mode and the third mode are the same with one main difference being the scattering estimation. Therefore, we can run the FDPM module 16 once before all CW measurements to correct for scattering effect. In the fourth mode, which is the slowest method, the FDPM module 16 and CW module 22 are interleaved to take consecutive measurements. Scattering information will be provided in all measurements. Therefore, this fourth mode provides the most accurate quantitative information for all four tissue components (Water, Lipid, Deoxy-Hb, and Oxy-Hb). A summary of modes and relative application is summarized in Table 1 showing the four modes, the intended application of each mode, the data acquisition rates and number of different wavelengths used in the data acquisition.

TABLE 1

DOSI Modes and Applications

| Modes | Applications | Rate (Hz) | Wavelengths |
|---|---|---|---|
| FDPM + CW | Full Recovery of Scattering in All Measurements | 0.5-1 | 4-6-8 |
| FDPM | Quantitative Monitoring of Blood Components | 0.5-0.8 | 4 |
| Baseline FDPM + CW | Constant Scattering Assumption Available-Quantitative & Rapid Measurements- (Fast Scanning-Hemodynamic Monitoring) | 40-250 | 2-4 |
| CW | Monitoring Rapid Changes in Hemodynamic | 80-250 | 2-4 |

Integration with Tracking Sensors

Figure 5:
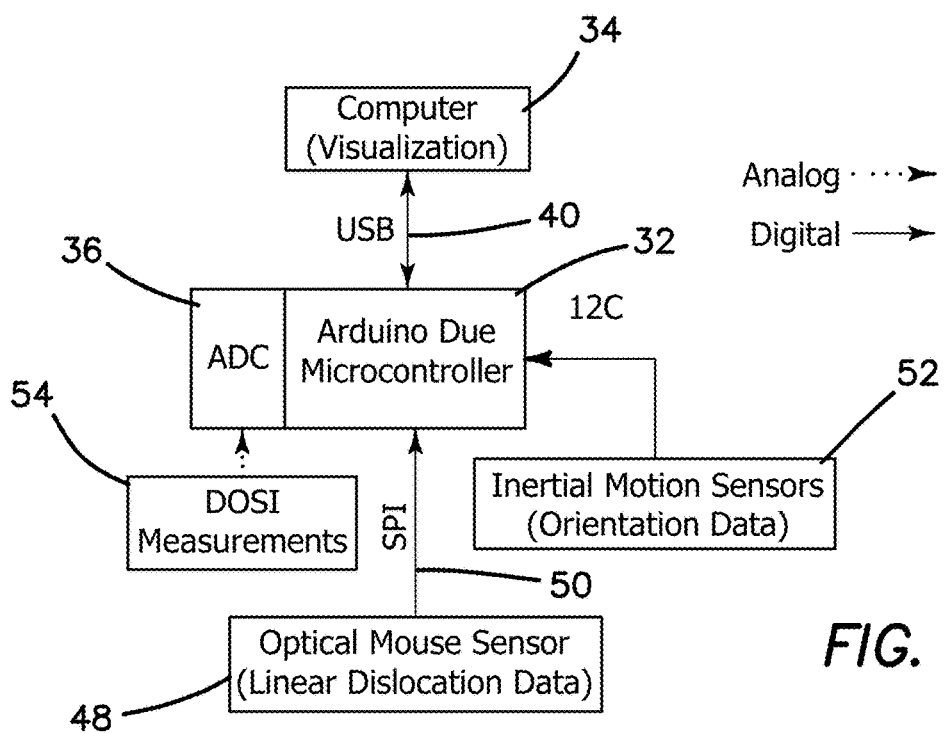
FIG. 5 is a block diagram of the DOSI and tracker subsystem integration included in the apparatus of FIG. 4.

The CW fast measurements require a tracking subsystem to record the displacement of the DOSI probe on the two dimensional tissue surface. We employed two sensors to quantify the measurements' path. In the following and as seen in the block diagram of FIG. 5, integration of these sensors with the DOSI system will be explained.

Linear Displacement

An optical mouse 48, IC ADNS-9800 (Avago Technologies, San Jose, Calif., United States), was utilized to measure the linear displacement of the DOSI probe 52 including lasers 12, 18 or corresponding optical fibers coupled thereto (not shown) coupled thereto and is connected to microcontroller 32 through a serial peripheral interface (SPI) 50. The mouse 48 includes a low resolution detection chip designed for high speed data transfer and a vertical cavity surface-emitting laser (VCSEL) that illuminates 0.5 mW at 840 nm. Light reflection from the surface of the tissue 24 is imaged on to the detector chip where displacement information is calculated from reflected image by an embedded digital signal processor. The mouse 48 can support a frame rate of 12,000 frames per section at a resolution up to 8200 counts per 2.54 cm (1 inch). The motion detection is up to 381 cm (150 inches) per second at an acceleration of up to 30 g.

Rotational Displacement

Three inertial motion sensors 52 were utilized to quantify the rotational displacement of DOSI imaging probe 54. Inertial sensors 52 comprise a nine degree of freedom sensor stick from Sparkfun (Denver, Colo., USA) contains an ADXL345 accelerometer (Analog Devices, Norwood, Mass. USA), HMC5883L compass (Honeywell, city state USA), and ITG-3200 gyroscope (Invensense, San Jose, Calif. USA). The accelerometer chip is capable of measurements up to +/−16 g's with 10 bits of resolution, the gyroscope can measure up to +/−2000 degrees with 16 bits of resolution, while the magnetometer chip has a 12 bit resolution that can sense up to 8 gauss.

A sensor fusion algorithm based off open source software, altitude and heading reference system, processes the raw data output of each of these sensors 52. From the same open source, a modified version of sensor calibration procedure was also utilized. The method that merges the data is a directional cosine matrix (DCM) algorithm, which is a simplification of a Kalman Filter. The directional cosine matrix first computes the magnetic heading. Then the algorithm normalizes the three directional matrices to enforce orthogonality that may be off, caused by numerical error. The error is estimated and corrected for roll and pitch drift based on the accelerometer, while yaw drift error is based on magnetic heading. Based on the three inertial motion sensors, the orientation of the probe 54 can be estimated using the DCM algorithm.

Figure 6:
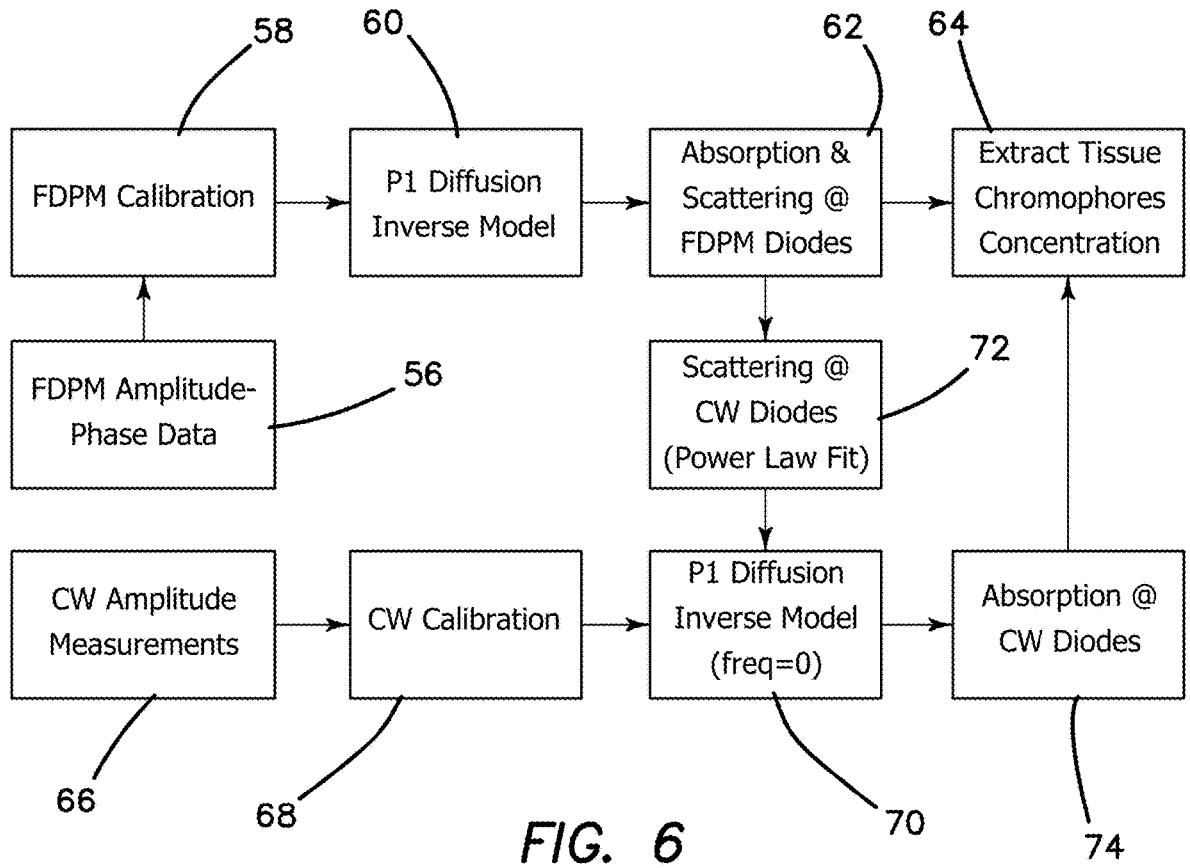
FIG. 6 is a flow diagram of the combined FDPM and CW operation of the apparatus of FIG. 4.

The overall process of data analysis is shown in the block diagram of FIG. 6. The FDPM module 16 separates absorption (pa (A)) from reduced scattering (p's (A)) at the laser diode wavelengths via measuring amplitude changes and phase shifts over a 50-300 MHz frequency bandwidth. FDPM amplitude and phase data is collected at step 56. Measurements are affected by the system components' response such as the RF cables, RF switches, and optical fibers. Thereby, objects with known optical properties (tissue-simulating phantoms) are used as references to remove the inherent response of the instrument from measurements in calibration step 58. Optical properties are recovered via fitting calibrated data to the $P_1$ diffusion approximation to radiative transfer equation (RTE) for light propagation in turbid media with semi-infinite boundary conditions at step 60 to calculate the reduced absorption and scattering coefficients at step 62.

The scattering values measured at FDPM diodes 12 enable us to obtain the scattering spectra across the 650-1000 nm range. The FDPM scattering coefficients are fit to a power law according to the Mie theory, and scattering coefficient can be interpolated and extrapolated at the CW wavelengths: $\mu_s'(\lambda) = a\lambda^{-h}$. at step 62. From the reduced coefficients, the tissue chromophore concentrations can be extracted at step 64.

As also seen in FIG. 6, CW amplitude measurements collected at step 66 need to be calibrated at step 68 in a similar manner to FDPM amplitude data. With estimated scattering coefficients at CW laser diodes 18, the CW data is fed to the same model used for FDPM measurements at step 70 to extract absorption coefficients (measurement frequency is set to zero and phase shifts are discarded). Scattering coefficients are determined from step 62 and fit to a power law for use in the P1 diffusion inverse model computation at step 70. Absorption coefficients at the CW diodes 18 are then computed at step 74. In the final step 64, tissue components concentration will be extracted from absorption coefficients at FDPM diodes 12 and CW diodes 18.

Performance Comparison of DOSI Systems Using CWFD and SSFD

Two different measurements were performed in-vitro (phantom study) and in-vivo (abdomen tissue mapping) to validate and characterize the instrument (CWFD) performance in recovering optical properties and tissue chromophore concentrations. The results were compared to those provided by the previous generation of DOSI systems (SSFD).

Figure 7A:
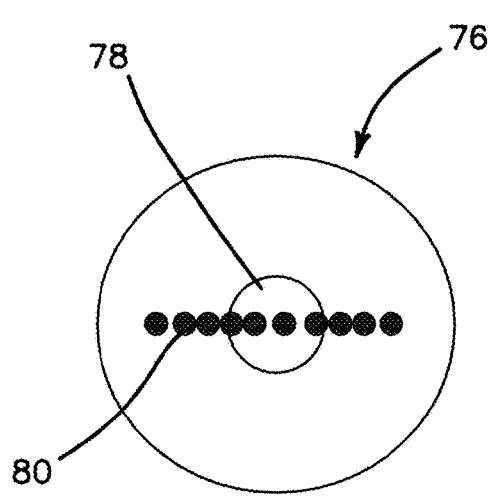
FIG. 7a is a top plan view of a phantom of a tumor in a tissue block.
Figure 7B:
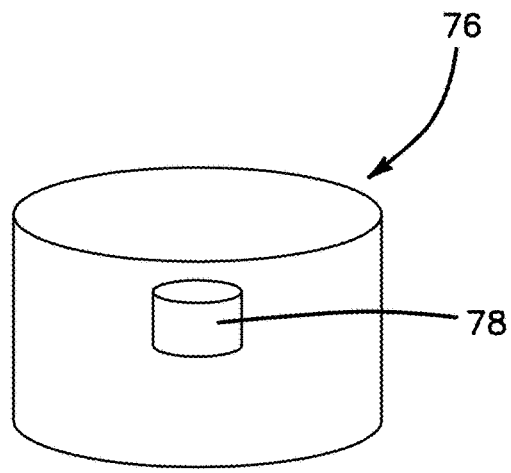

A tissue-simulating (breast) phantom 76 was measured with an embedded tumor 78 1 cm beneath the surface seen in FIGS. 7A and 7B with both CWFD of the illustrated embodiments and SSFD of the prior art. The rationale behind this study was to test and compare the new platform ability in extracting optical properties equivalent to those measured by steady-state Fourier domain (SSFD) technology. FIG. 7A depicts the location of measurements which is a line-scan with nine discrete points 80. The locations should be selected in a way that they cover a different range of absorption optical properties. To achieve this, we measured 10 spots starting at locations with low absorption (background) and adequate distance from tumor 78, and then moved the probe with a step of 7 mm toward the tumor position and continued the measurements to pass the tumor 78. For more accurate results, we used the same source-detector separation (22 cm) for both instruments, and repeated these measurements three times on each point 80. Phantoms absorption coefficients at four wavelengths (880 nm, 904 m, 915 nm, and 975 nm) recovered using both systems in three trials are summarized in Table 2.

TABLE 2

Phantom Opitcal Properties Comparison

| | Absorption Difference | | |
|---|---|---|---|
| Location | Mean | Min | Max |
| Background | 3.6% | 1.3% | 4.9% |
| Tumor | 4.2% | 2.7% | 5.8% |

These results shows CWFD has similar performance to SSFD which means it has the capability of recovering different ranges of optical properties with the same performance as previous SSFD technology (less than 6% difference).

In-Vivo Measurements

The degree of biological tissue inhomogeneity is significantly higher than encountered in phantoms. Therefore, an ultimate test to show equivalency between both CWFD and SSFD systems would be a tissue measurement. We chose the abdomen tissue for this purpose, since breast cancer patient measurements were unavailable due to the CWFD system packaging. Based on the fact that one of main goals for adding CW modality to the FD technology was to increase the spectral bandwidth above the 880 nm region, characterization and recovery of abdomen tissue lipid and water content can be a proper platform to compare both approaches.

Figure 8:
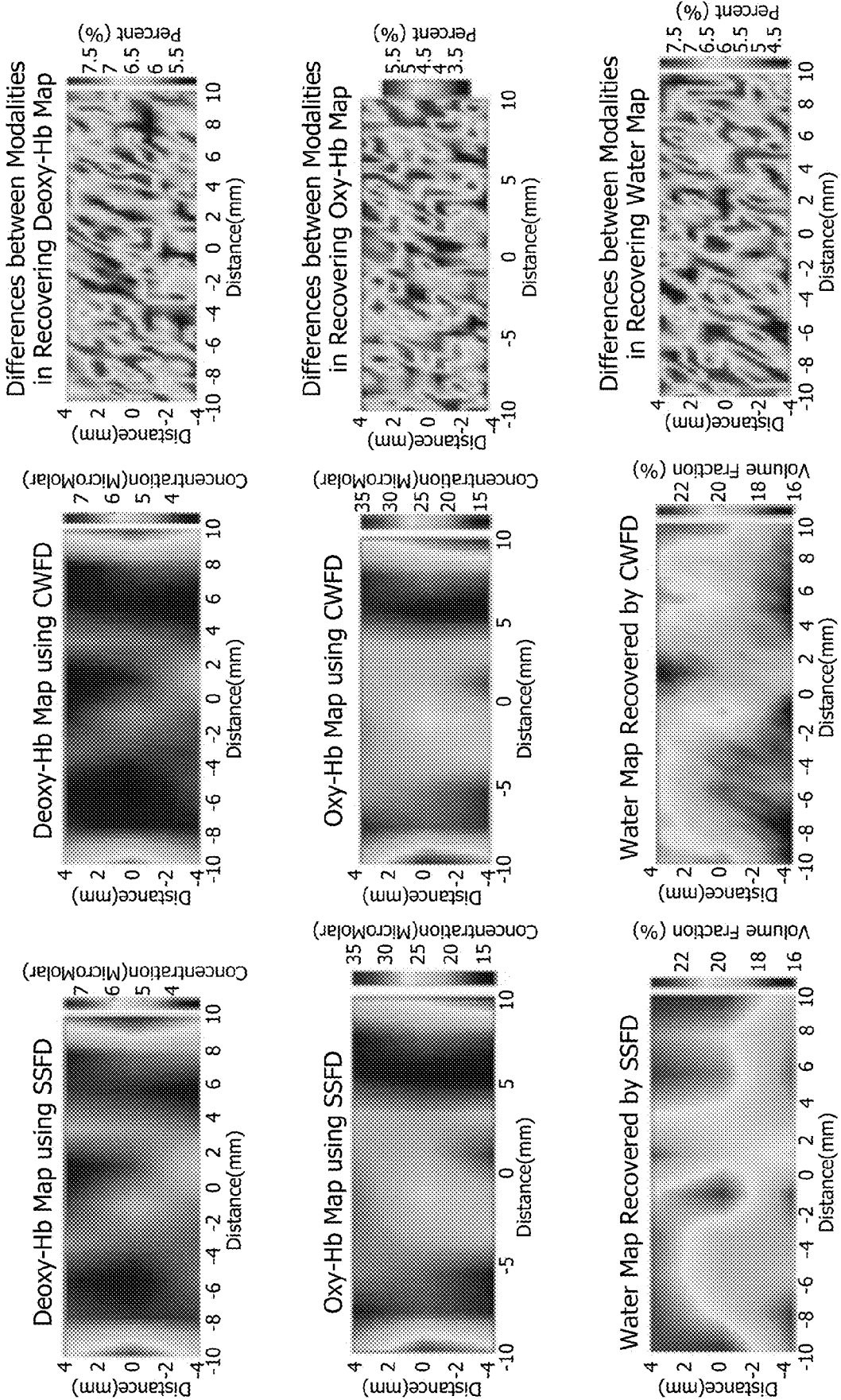
FIG. 8 is a collection of color coded data maps of human abdomen scans of the chromophores: deoxy-Hb, oxy-Hb, water, lipid and TOI from the top row to the bottom row respectively. The left column are maps of the above chromophore concentrations using SSFD and the middle column are maps of the chromophore concentrations using the CWFD of the illustrated embodiments. The right column are maps of the percentage differences between the measured concentrations of the chromophores in the first column using SSFD and in the second column using CWFD.
Figure 8:
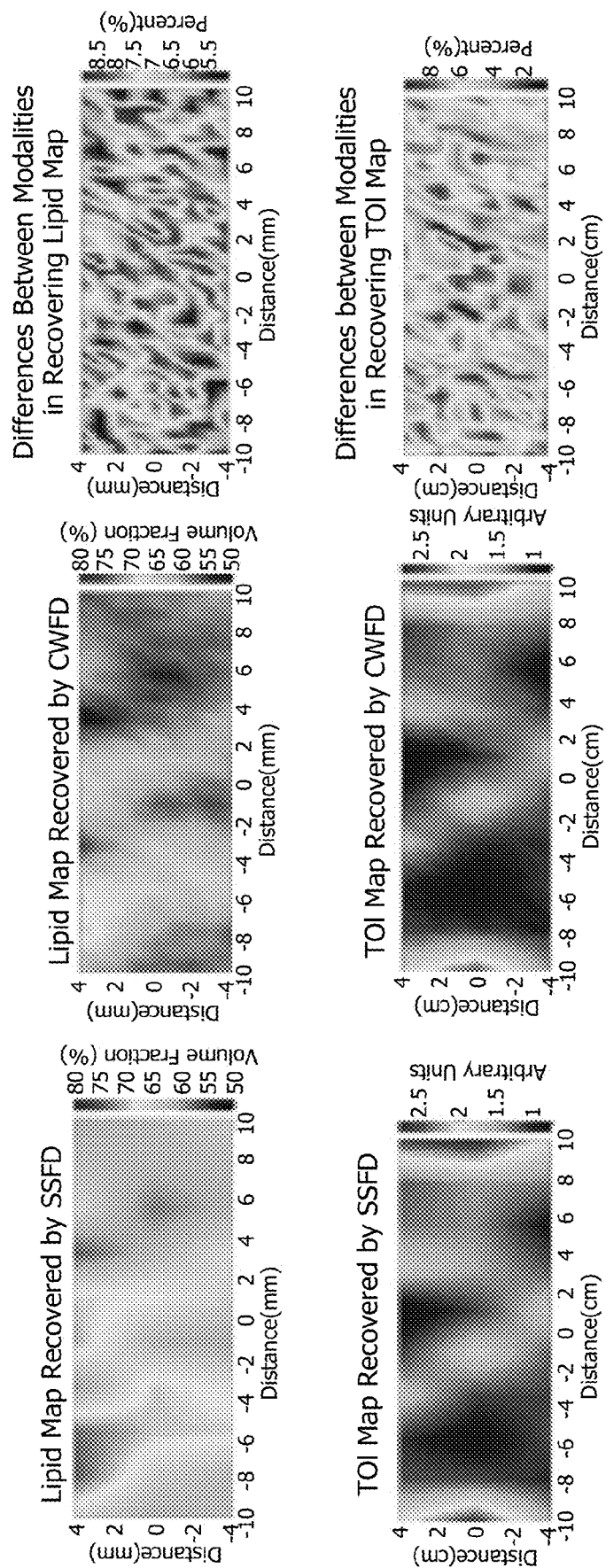

We measured a 3 cm×10 cm rectangle area on abdomen tissue with both systems. We marked the tissue with thirty points in a grid pattern with 1 cm spacing among adjacent points centered on subject's umbilicus. For more accurate results, we used the same source-detector separation (22 cm) for both systems, and repeated these measurements three times on each location and averaged the extracted absorption coefficients before fitting for tissue chromophores. FIG. 8 shows abdomen tissue DOSI image maps measured with both systems. The top line of FIG. 8 is comprised of three ±4×±10 cm color coded maps of the micromolar concentration of Deoxy-Hb using SSFD, Deoxy-Hb using CWFD and the differences in the modalities in recovering Deoxy-Hb in percentages respectively. Similarly the second line of FIG. 8 is comprised of three ±4×±10 cm color coded maps of the micromolar concentration of Oxy-Hb using SSFD, Oxy-Hb using CWFD and the differences in the modalities in recovering Oxy-Hb in percentages respectively. The third line of FIG. 8 is comprised of three ±4×±10 cm color coded maps of the volume fraction percentage of water using SSFD, water using CWFD and the differences in the modalities in recovering water in percentages respectively. The fourth line of FIG. 8 is comprised of three ±4×±10 cm color coded maps of the volume fraction percentage of lipid using SSFD, water using CWFD and the differences in the modalities in recovering lipid in percentages respectively. The fifth line of FIG. 8 is comprised of three ±4×±10 cm color coded maps of the measured TOI in arbitrary units using SSFD, TOI using CWFD and the differences in the modalities in TOI in percentages respectively. Good agreement between the two modalities can be seen.

We also calculated the percent difference between maps at each pixel and summarized them in the Table 3. The largest difference is found in the TOI variable (9.7%) while Oxy-Hb has the lowest error (3%).

TABLE 3

Adbomen Chromophore Error Analysis

| Chromophore | Error Range |
|---|---|
| Lipid | 5-9% |
| Water | 4-8% |
| Deoxy-Hb | 5-8% |
| Oxy-Hb | 3-6% |
| TOI | 0.6-9.7% |

Real-Time Scanning

Figure 9A:
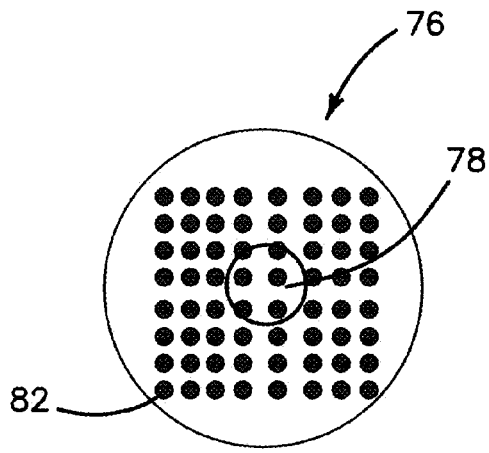
FIG. 9a is a diagram of the phantom of FIGS. 7a and 7b scanned with a grid pattern by SSFD with the resulting color coded data map of FIG. 9c.
Figure 9B:
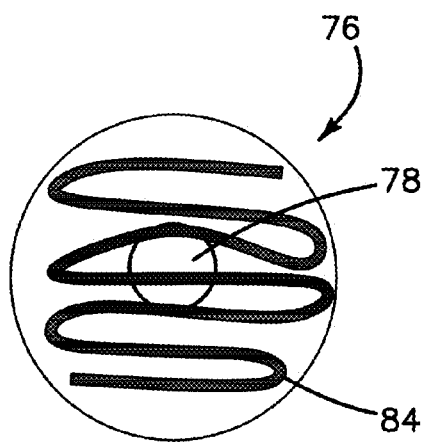
FIG. 9b is a diagram of the phantom of FIGS. 7a and 7b scanned with a continuous curved path by CWFD with the resulting color coded data map of FIG. 9d.
Figure 9C:
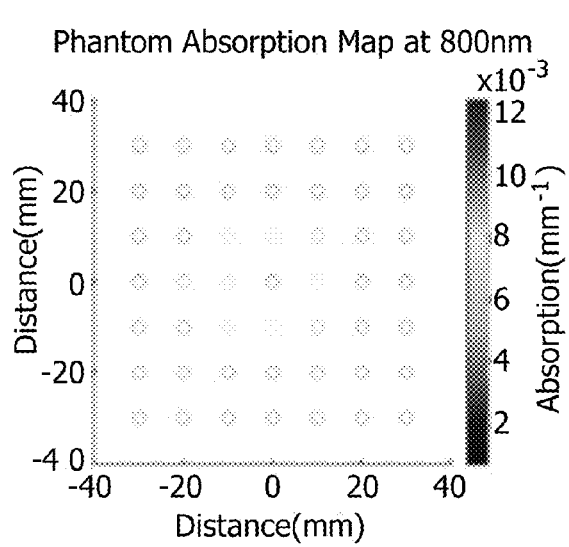
Figure 9D:
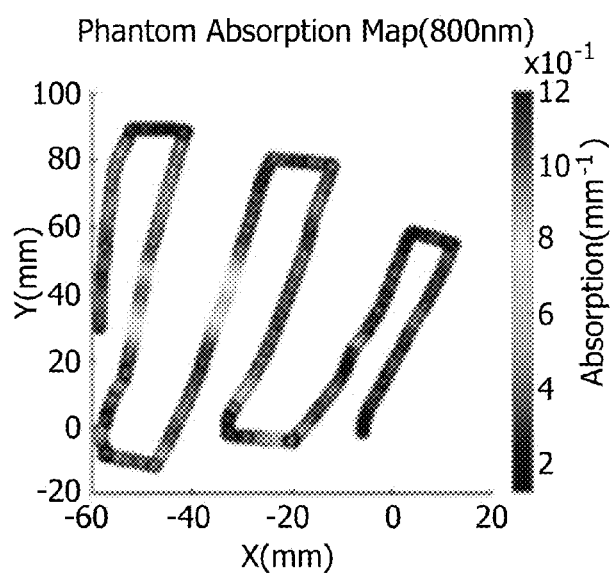

We scanned a phantom with an embedded inclusion with both SSFD and CWFD systems. We used a 22 mm source detector spacing for both instruments. SSFD measurements were taken on 49 different points 82 on a 7 cm×7 cm grid pattern with 1 cm distance between adjacent points as seen in FIG. 9a. For CWFD measurements, we took advantage of the system's high temporal resolution and tracking ability and high density measurements to scan the phantom continuously at 40 HZ with four CW wavelengths (800 nm, 880 nm, 904 nm and 980 nm) in a curved path 84 as depicted in FIG. 9b. CW measurements are corrected with a baseline FD measurement. The absorption maps at 800 nm from both approaches are shown in FIGS. 9c and 9d, respectively. It took 30-40 minutes to measure the phantom at 49 points 82 (pixels) with SSFD system while the CWFD instrument measures the same area with 1518 points on path 84 took less than 20 seconds.

Figure 10A:
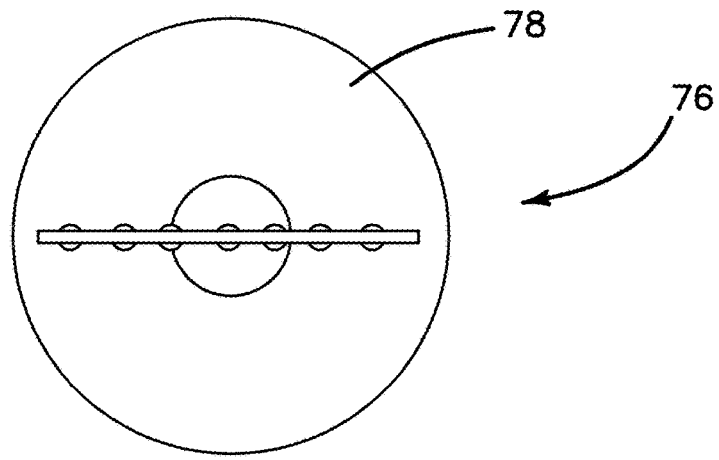
FIG. 10a is a diagram of the phantom of FIGS. 7a and 7b scanned on a line of points using SSFD and CWFD with the resulting color coded data absorption map of FIG. 10b and in a shifted line of points using SSFD and CWFD with the resulting color coded data absorption map of FIG. 10c showing the difference point shifted sampling makes in the case of SSFD, but not CWFD.
Figure 10B:
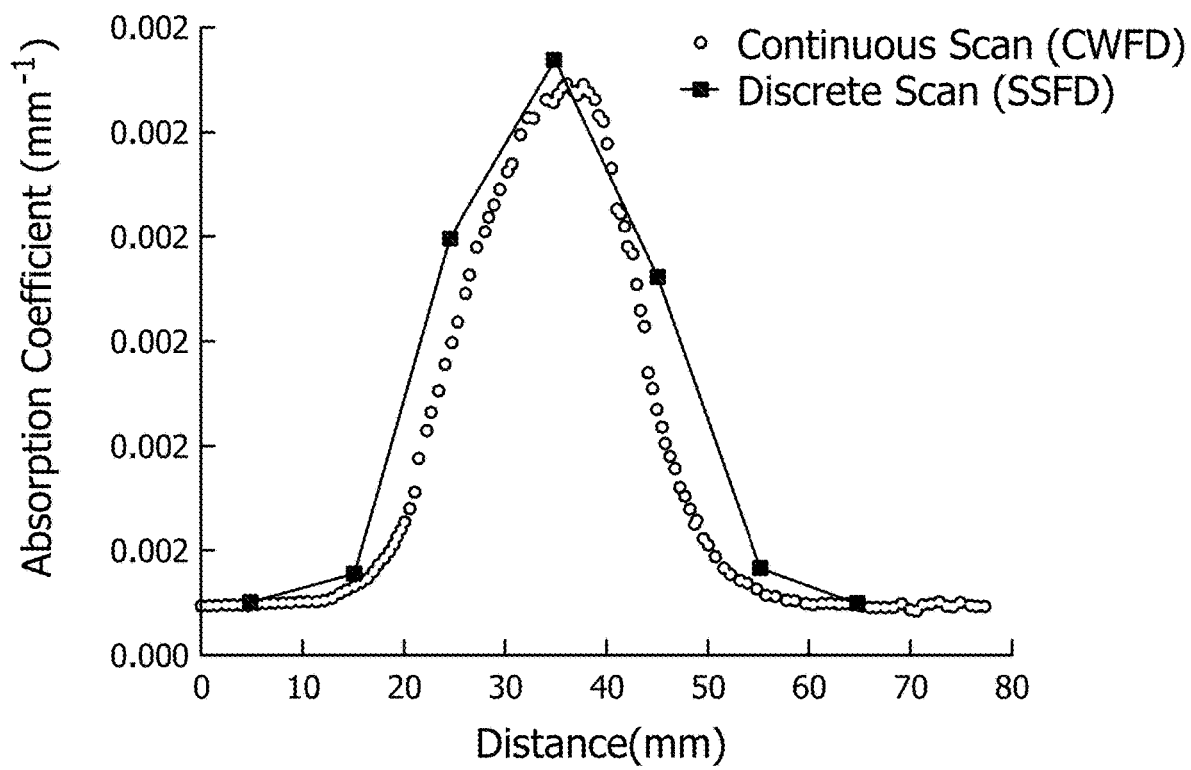
Figure 10C:
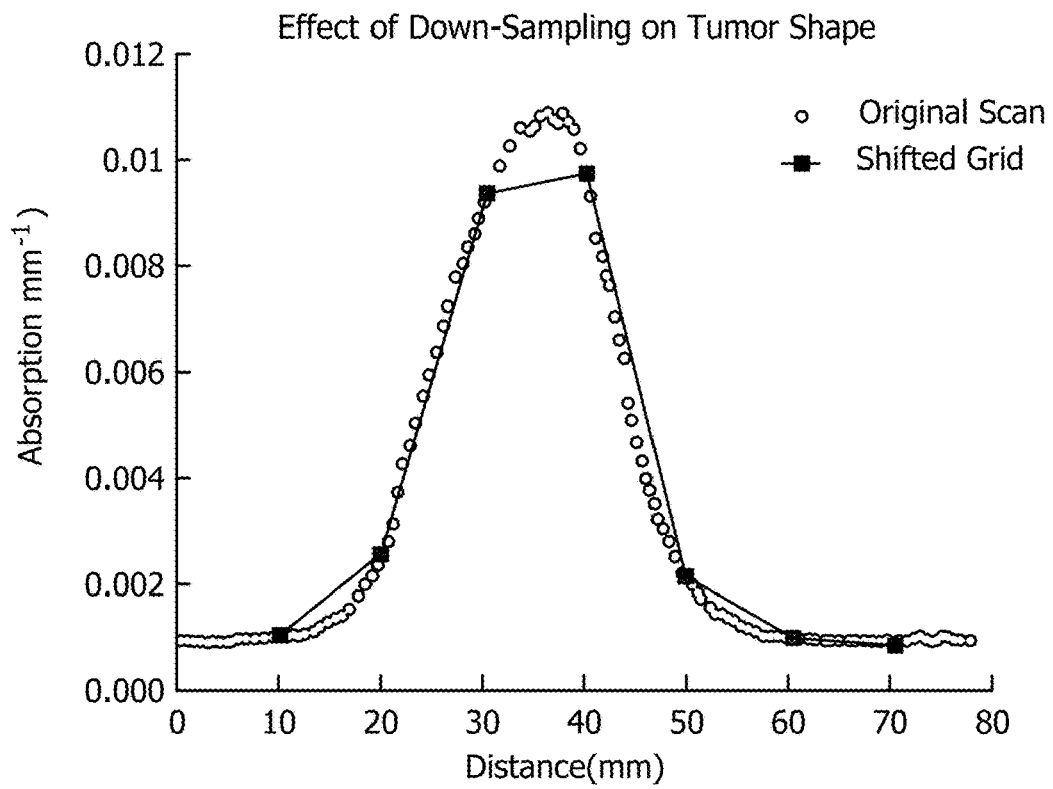

In order to compare the two methods in more detail and characterize their differences, we looked at cross-section line-scans in one dimension as seen in FIGS. 10a-10c. We plotted the absorption coefficients as a function of distance along a line-scan 86 over the tumor 78 for both instruments as seen in FIGS. 10b and 10c, respectively. As we expected, high temporal and density measurements by CWFD system improves the imaging dramatically. It is to be expressly understood that different grid patterns or different scan paths other than those explicitly shown herein may be used without departing from the original spirit and scope of the invention. We down sampled the CWFD data to simulate and investigate the effect of grid variation on the tumor absorption shape. Comparison of the SSFD grid measurements of FIGS. 10b and 10c show that slight variations in SSFD grid patterns will result in significant changes in recovered tumor shape.

Figures 12A, 12B, 12C:
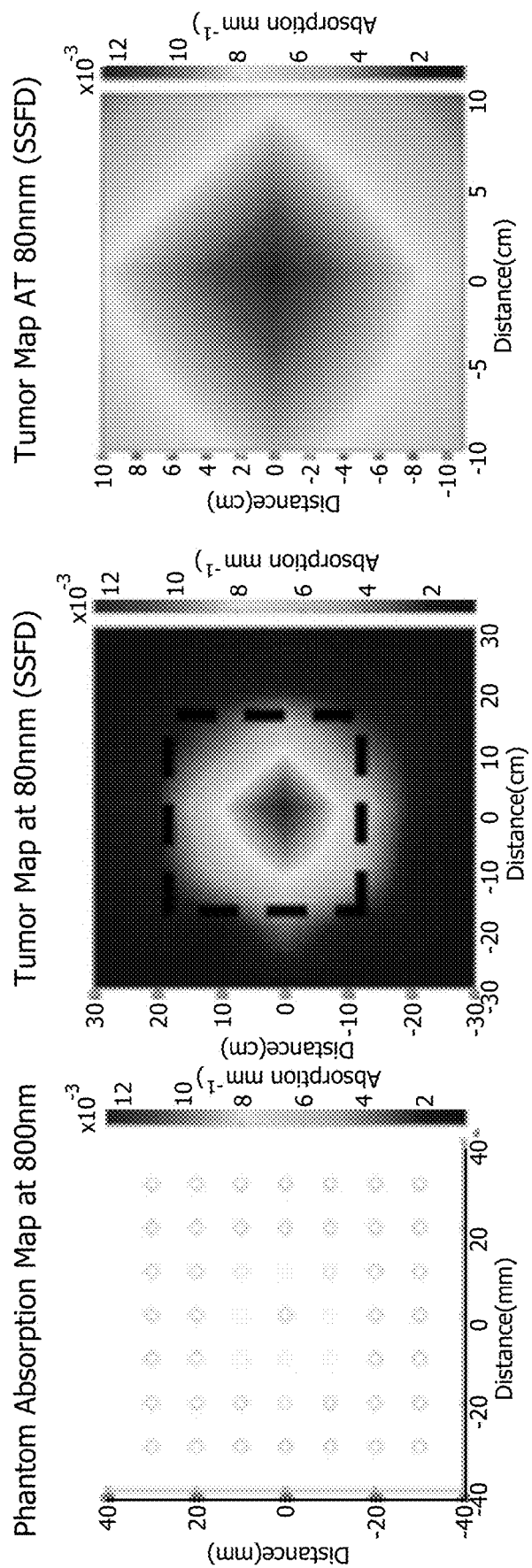

In order to improve CWFD data, we defined a region of interest (ROI) 92 in CWFD first scan path 88 seem in the color coded graph of absorption as a function of position FIG. 11a. A grid scan at 800 nm was made using SSFD and is depicted in the color coded map of FIG. 12a. We rescanned over the tumor region continuously multiple times in a scan path 90 to obtain high density color coded measurement over the ROI as seen in FIG. 11b. As discussed above, DOSI images are produced by interpolation of data obtained from grid patterns. We interpolated both SSFD images in FIG. 12c and CWFD images in FIG. 11c to compare their performance in recovering overall tumor shape. As it was expected, the SSFD system has a lower resolution due to its inability to take continuous measurements. The interpolation algorithm attempts to estimate absorption among measurements every 10 mm which results in sharp edges as depicted in the substantially diamond shaped rendition in FIGS. 12b and 12c. On the other hand, CWFD images are more uniform in tumor region since large number measurements were taken in the ROI 92 of FIG. 11c.

The analysis of tumor absorption dependency on grid pattern and interpolated images suggest that real-time scanning by CWFD modality provides higher resolution and more accurate maps in comparison to a SSFD method.

Additional Application of the Illustrated Embodiments

The above disclosed apparatus 10 can be used in a variety of in-vivo applications including the ability to recover a patient's heart rate from their fingertip, muscle, or brain. Additionally, in a separate embodiment, the system is used to continuously monitor the wrist and muscle hemodynamics changes induced by paced breathing and recovering respiration rates from blood chromophores. In an additional embodiment, the system is used to characterize the arm vasculature reactivity during arm cuff occlusion.

Tissue Oximetry

Figure 13:
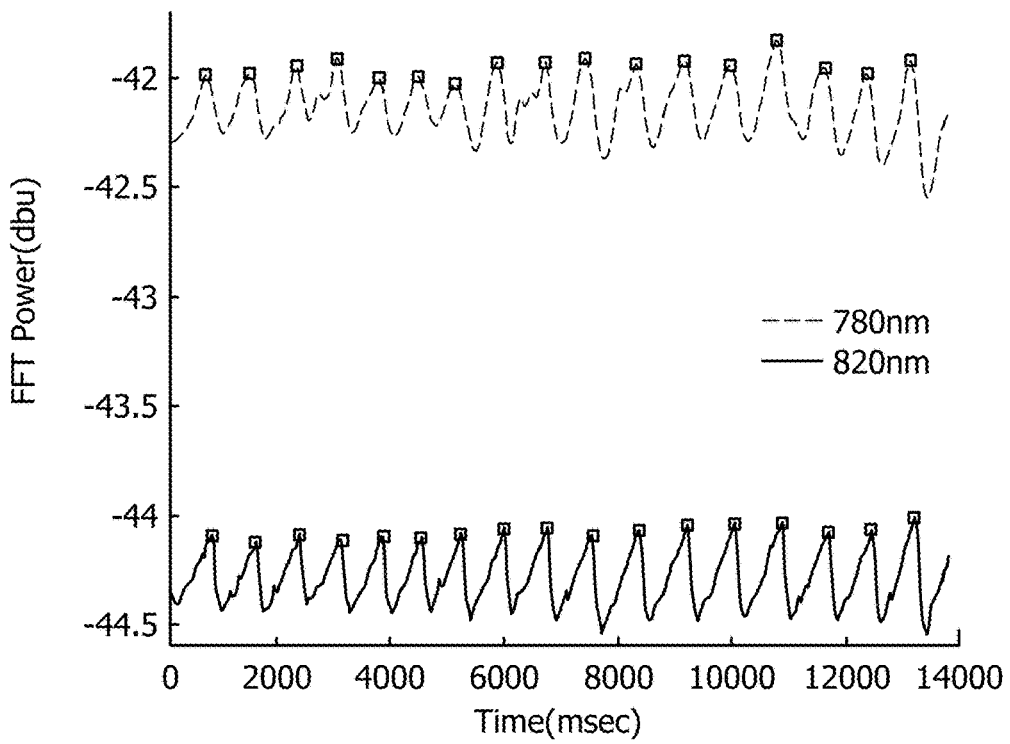
FIG. 13 is a time graph of raw absorption data taken from a fingertip using CWFD with two lasers operated at 780 and 820 nm for tissue oximetry of oxy-Hb and deoxy-Hb showing heart rate of a human subject.

In a first embodiment, the apparatus 10 is used to extract the heart rate from the fingertip, which is also a common target for pulse-oximetry instruments. The raw data from the left index finger, where two laser diodes (780 nm and 820 nm) were used in FDPM module 16 and/or CW module 18 and data recorded at sample rate of 250 Hz is shown in FIG. 13. The wavelengths of the laser diodes were selected below and above the isosbestic point (810 nm) where both deoxygenated hemoglobin and oxygenated hemoglobin have the same absorption coefficients. As our control, we used a commercial system that was placed on the index finger of the right hand. We calculated the heart rate from raw optical and oxygenated hemoglobin concentrations signals with two different approaches. First, we ran a peak searching algorithm to find the corresponding peak in the photoplethysmogram (PPG) signal and divide the number of peaks by measurement duration to obtain an average per second, and then multiplied by 60 to get hear rate in beat per minute unit (bpm). We used an empirical mode decomposition (EMD) algorithm to remove motion artifacts and noise from data.

We developed an algorithm that can find peaks within a certain distance which is feasible for physiological parameters. There are reasonable thresholds for minimum and maximum distances between consecutive peaks. For instance, peaks with more than 2 seconds (30 bpm heart rate) or less than 0.3 seconds (200 bpm heart rate) are not possible. As seen in the FIG. 13, the algorithm found 17 peaks for both diodes during fourteen seconds of measurements which corresponds to 72.8 bpm (~73 bpm).

Figure 14A:
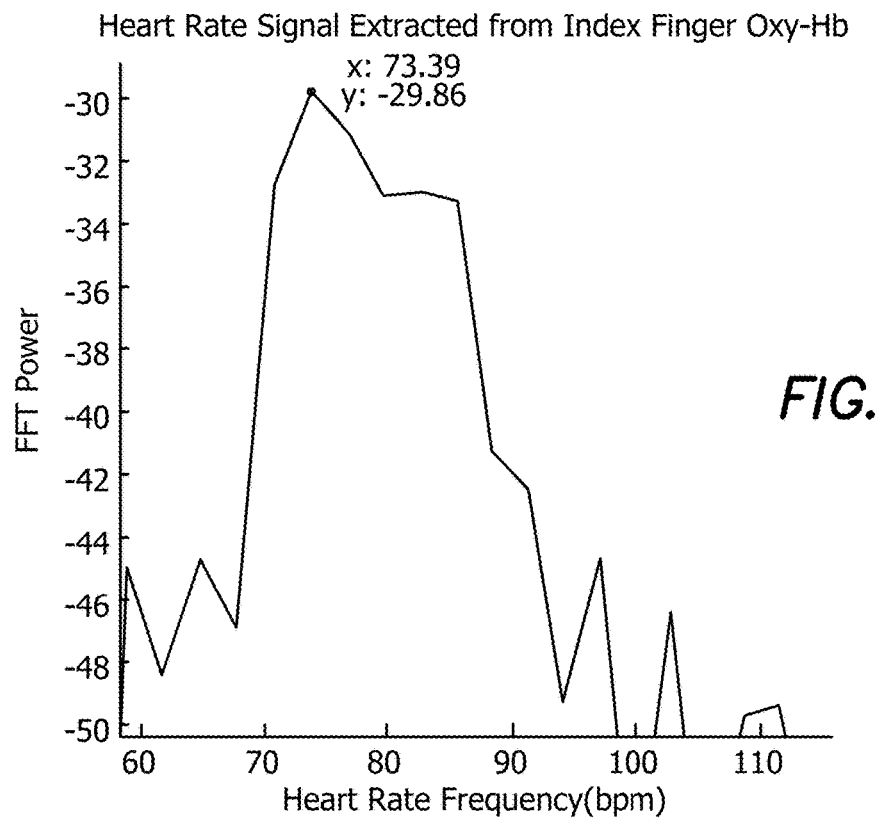
FIG. 14a is a FFT spectrum of the data of FIG. 13 as a function of heart rate frequency of bpm.
Figure 14B:
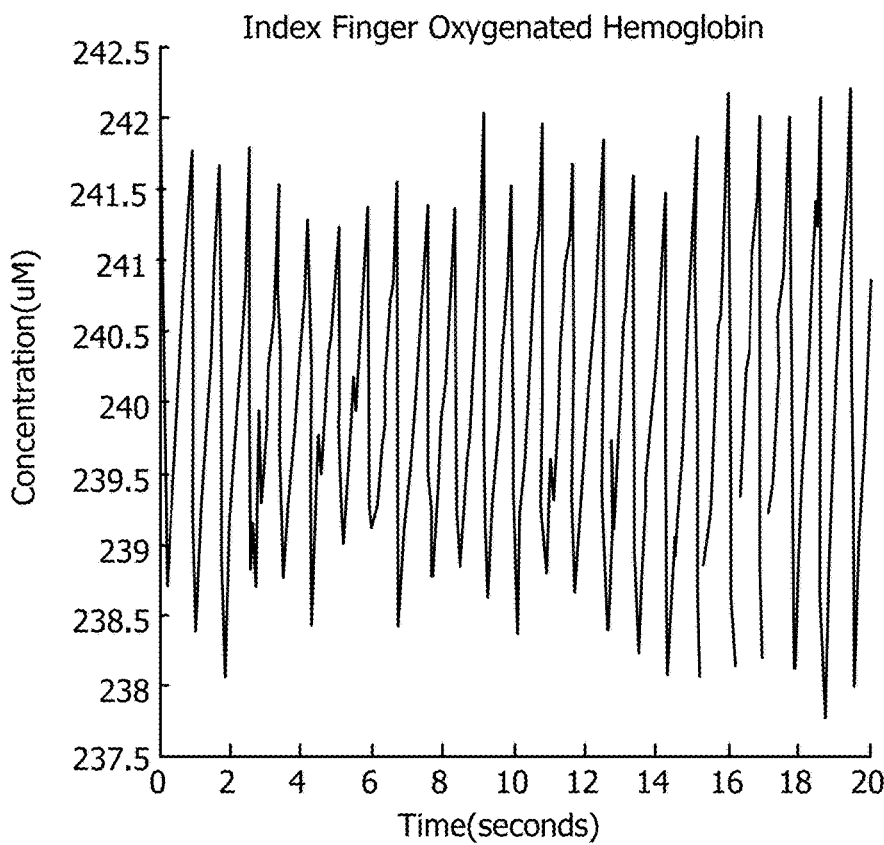
FIG. 14b is a time graph of the oxy-Hb in μM of the data of FIG. 13.

In a second algorithm, we applied a fast Fourier transform (FFT) on oxygenated hemoglobin concentrations and obtained a frequency peak at 73.4 bpm (~73 bpm) as seen in FIG. 14a. The measured oxygenated-Hb in µM as a function of time is shown in FIG. 14b. The commercial system reported the heart rate to be 74-bpm.

Next, we used the second approach (FFT) on wrist and brain (frontal cortex) tissue with 2 and 3 cm source-detector separations, respectively. The reason for choosing larger source-detector spacing for brain tissue is because of the presence of the skull.

Figure 15A:
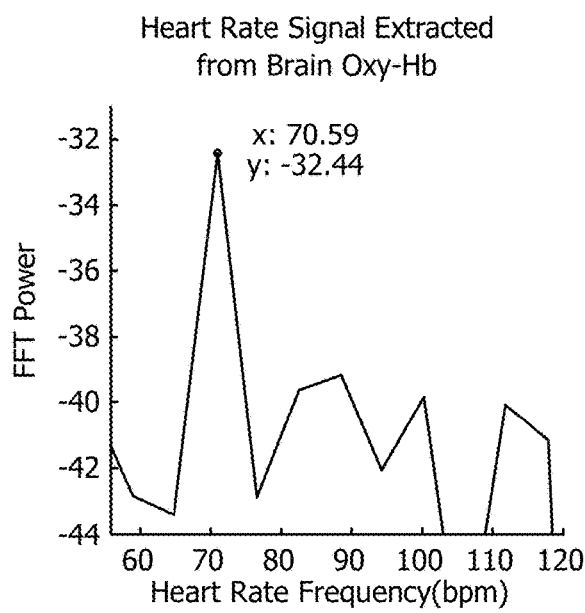
FIG. 15a is a FFT spectrum of heart rate extracted by CWFD from the brain of a human subject of oxy-Hb absorption data.
Figure 15B:
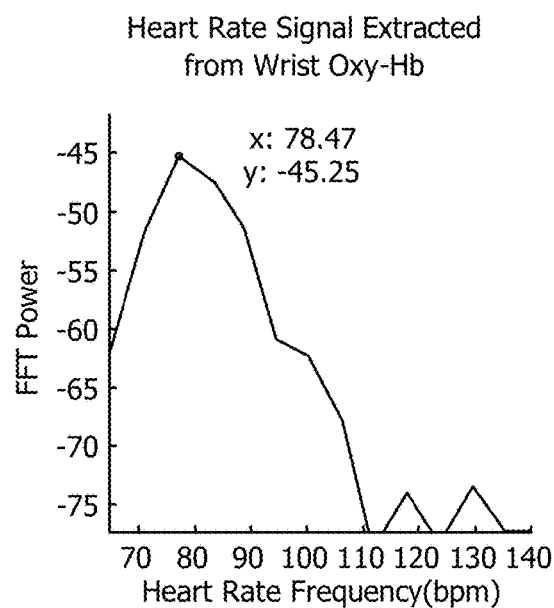
FIG. 15b is a FFT spectrum of heart rate extracted by CWFD from the wrist of a human subject of oxy-Hb absorption data.
Figure 15C:
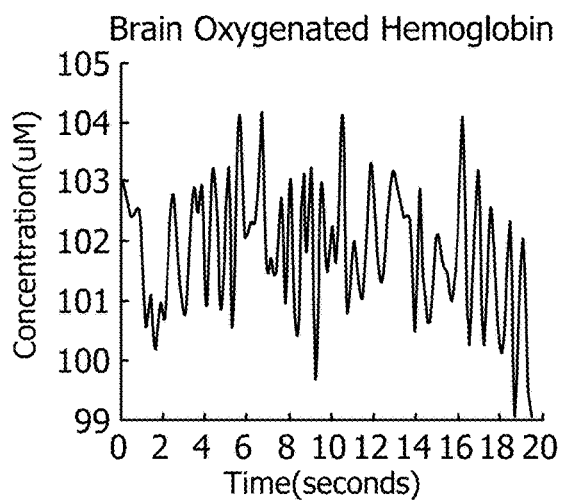
Figure 15D:
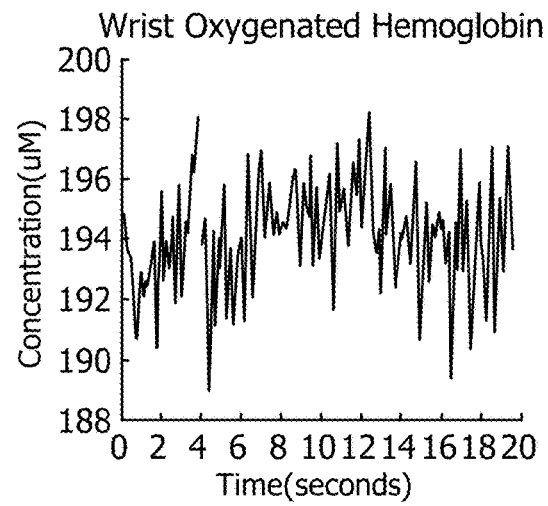
FIG. 15d is a time graph of the oxy-Hb in μM of the data of FIG. 15b.

Brain and wrist FFT analyses are depicted in FIGS. 15a and 15b, with accompanying brain and wrist oxyengenated-Hb in µM as a function of time shown in FIGS. 15c and 15d respectively. The system was able to extract the heart rate from different tissue sites accurately, which was validated with a commercial pulse oximeter. The following Table 4 summarizes all heart rates extracted by our system. The largest error belongs to the brain tissue which also has the highest signal attenuation.

TABLE 4

| Rate(bpm) Tissue | Fingertip | Wrist | Brain |
|---|---|---|---|
| CW System | 73 | 76 | 71 |
| Commercial System | 74 | 72 | 77 |
| Error | 1.35% | 5.55% | 6.49% |

Pace Breathing

In another embodiment, we continuously monitored and measured arm muscle and wrist hemodynamics during paced breathing for two reasons. First, we wanted to test the system's ability to recover respiration rate from thick tissues such as the wrist and arm. Second, we wanted to introduce a stimulus to the tissue hemodynamics and investigate corresponding vasculature reactivity caused by paced breathing. We asked subjects to control their respiration rate during measurements. Subjects were asked to breath-in over a period of two seconds and then breath-out over a period of 2 seconds (0.25 Hz) as the system was recording its measurements. To control the patient's breaths, they were shown a video clip with 0.25 HZ frequency instead of a metronome where they synchronized their respiration cycle to a visual signal with 0.25 Hz frequency (2 seconds inhale and 2 seconds exhale). An optical probe with 2 cm source-detector separation was positioned on the left wrist and left arm triceps muscle and the system was run at 80 Hz. Relative changes in oxygenated hemoglobin and deoxygenated hemoglobin concentrations were also calculated from four wavelengths 680 nm, 780 nm, and 800 nm and 820 nm, and from the absorption coefficients as seen from FIGS. 16a-16f.

Figure 16A:
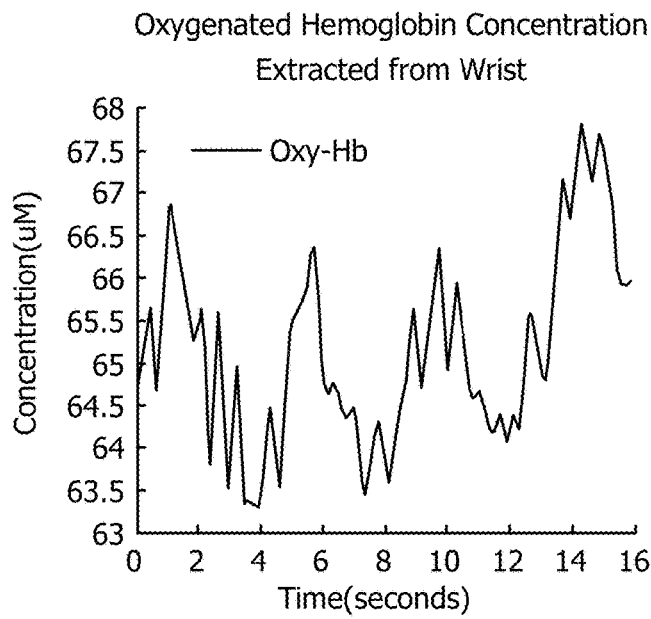
FIGS. 16a and 16d are time graphs of the concentration of oxy-Hb and deoxy-Hb in μM respectively from the wrist of a human subject extracted by CWFD.
Figure 16B:
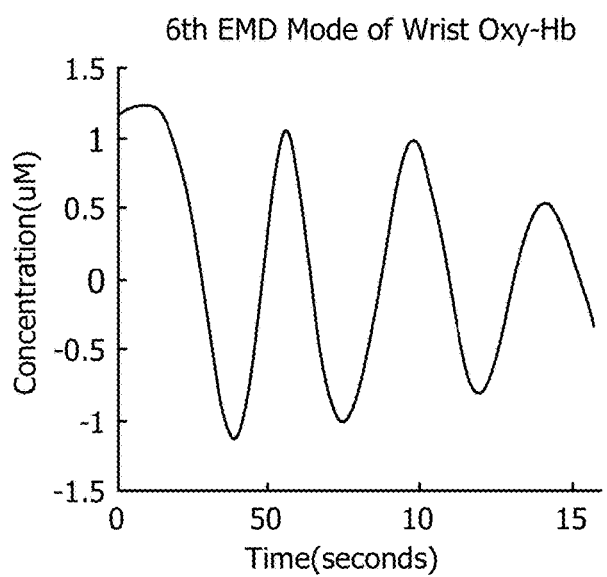
FIGS. 16b and 16e are time graphs of the concentration of oxy-Hb and deoxy-Hb in μM respectively from the wrist of a human subject extracted by CWFD in the $6^{th}$ EMD mode.
Figure 16C:
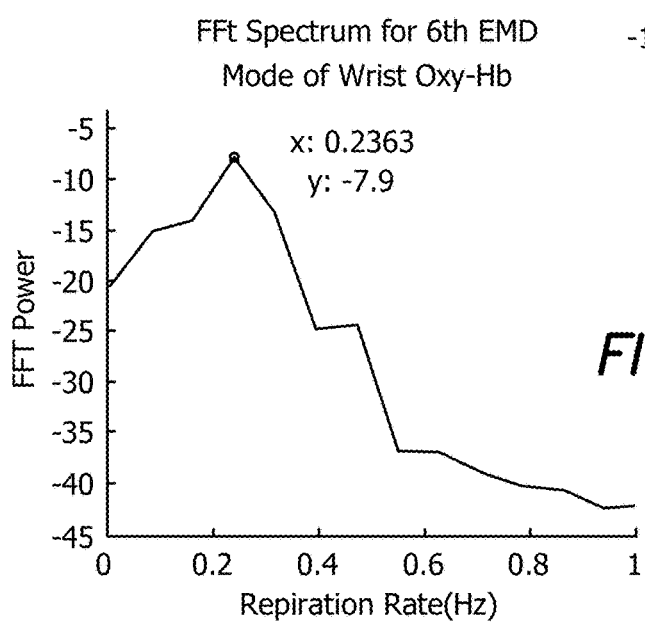
FIGS. 16c and 16f are FFT spectra of the concentration of oxy-Hb and deoxy-Hb as a function of respiration rates respectively from the wrist of a human subject extracted by CWFD for the $6^{th}$ EMD mode.
Figure 16D:
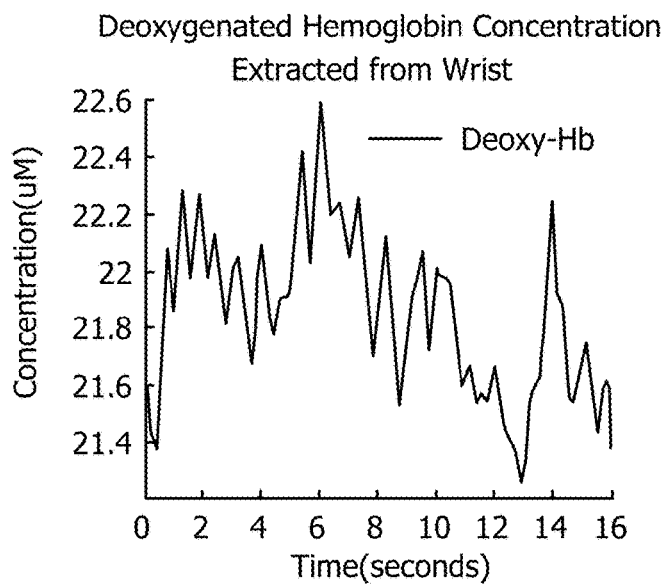

We applied an EMD algorithm to oxygenated and deoxygenated hemoglobin concentration time series as shown in FIGS. 16a and 16d respectively and extracted different underlying signals. The first few EMD modes (1-3) are usually noise data, and last EMD modes are generally motion artifacts and DC average. Physiological signals are usually embedded in the fourth (heart rate) to seventh EMD modes (respiration). Because of differences in physiology and subject motions, vital signal modes vary. This is why we combine the FFT algorithm with EMD modes to improve data analysis and visualization.

Figure 16E:
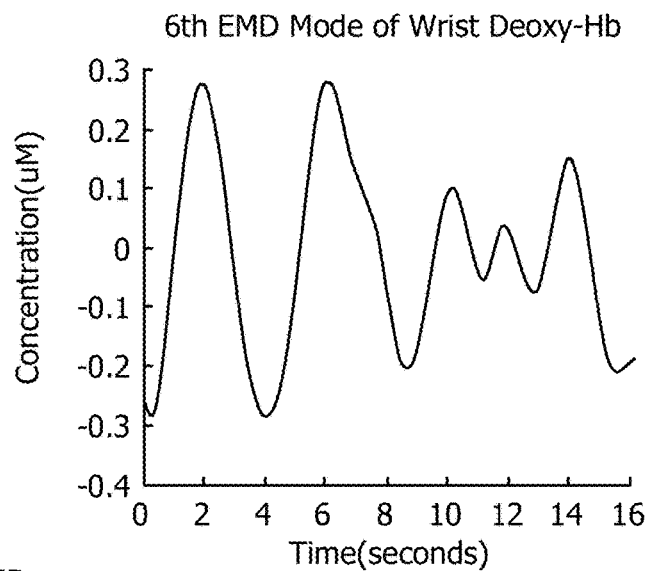
Figure 16F:
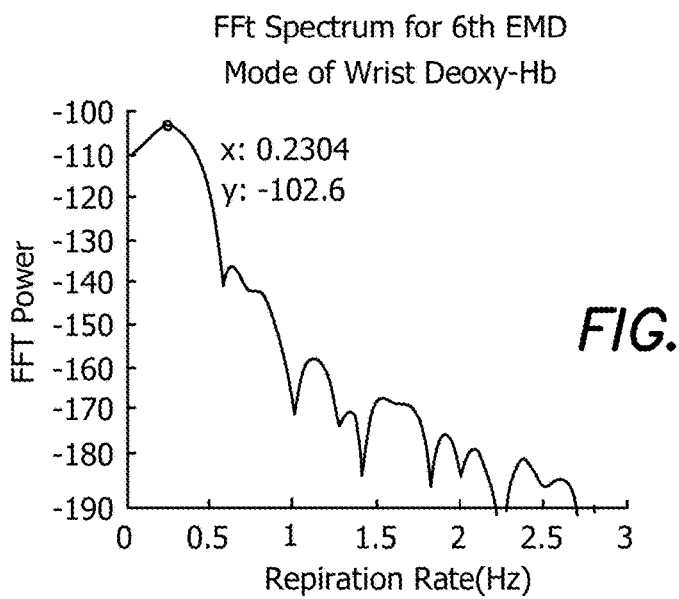

As seen in FIGS. 16a and 16d, the wrist blood chromophore concentrations extracted are shown over a sixteen second period. The first three EMD modes are subtracted from data to remove the noise. EMD modes are sorted according to frequency (from high to low). Since respiration frequency was 0.25 Hz, we would expect four respirations during the measurement (sixteen seconds total). The 6th EMD mode of wrist oxygenated and deoxygenated hemoglobin concentrations have exactly four peaks as seen in FIGS. 16b and 16e which correspond to the respiration events shown in FIGS. 16a and 16d respectively. We also applied an FFT algorithm to this $6^{th}$ EMD mode to obtain the respiration frequency. FFT power spectrums are shown in FIGS. 16c and 16f for oxy-Hb and deoxy-Hb respectively which have peaks at frequency of 0.235 Hz and 0.230 Hz for oxy-Hb and deoxy-Hb respectively. Both analysis methods recovered the same respiration rate for measurements.

Figure 17A:
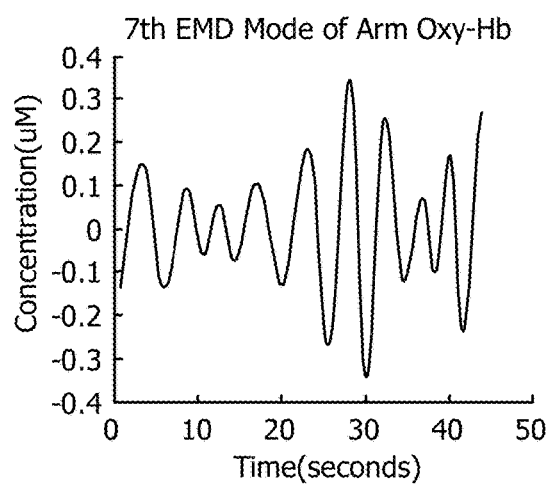
FIGS. 17a and 17c are time graphs of the concentration of oxy-Hb and deoxy-Hb in μM respectively from the arm of a human subject extracted by CWFD in the $7^{th}$ EMD mode.
Figure 17B:
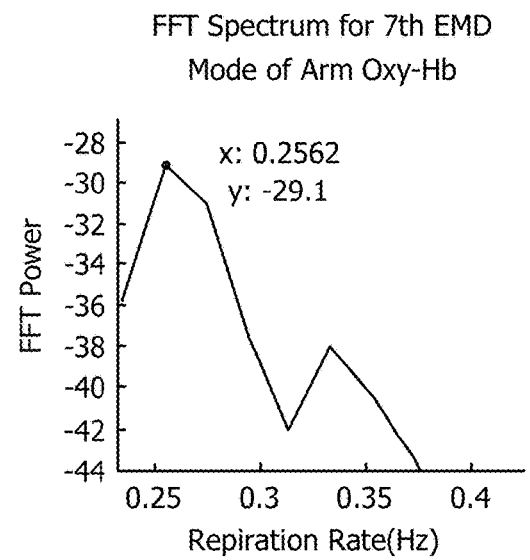
FIGS. 17b and 17d are FFT spectra of the concentration of oxy-Hb and deoxy-Hb as a function of respiration rates respectively from the wrist of a human subject extracted by CWFD for the $7^{th}$ EMD mode.
Figure 17C:
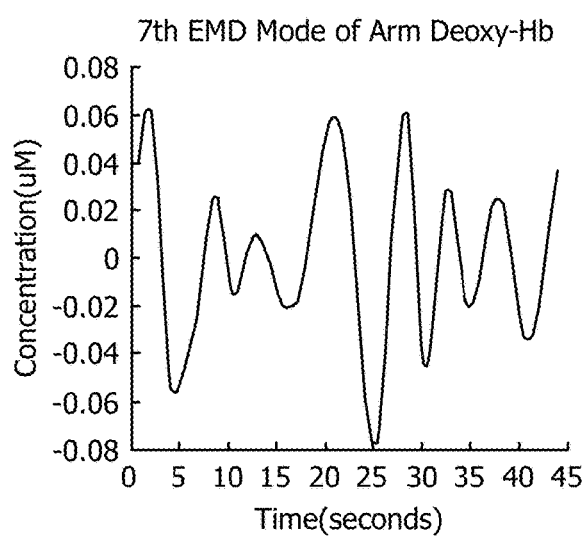
Figure 17D:
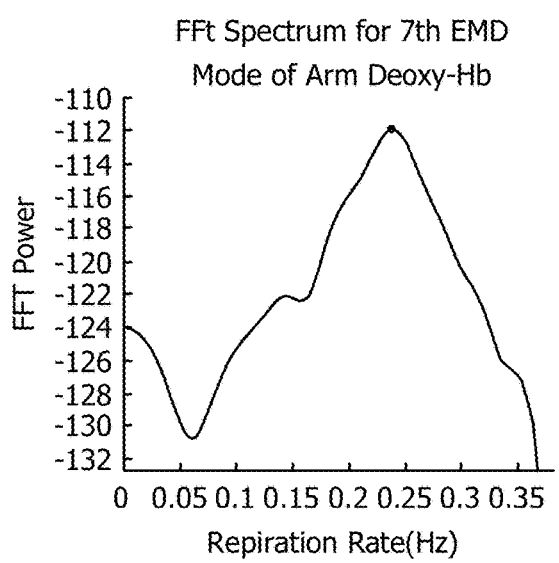

Next, we tried the same measurement on arm's triceps muscle with one difference, namely a longer measurement time. Instead of sixteen seconds of data collection, we recorded forty-four seconds of data. The corresponding EMD mode for respiration changed from the 6th to 7th EMD mode for arm oxygenated and deoxygenated hemoglobin in comparison to wrist data. The FFT algorithm recovered a 0.254 Hz peak for oxy-Hb as seen in FIG. 17b, and there were 10 peaks in EMD 7th mode time domain signal as seen in FIG. 17a. For deoxy-Hb, FFT algorithm finds 0.235 Hz shown in FIG. 17d while EMD 7th mode time signal shows 8 peaks in FIG. 17c. For both tissue sites, our instrument was able to recover respiration rates (0.25 Hz) induced by the stimulus (paced breathing) from accurately with both time domain (EMD) and frequency domain (FFT) algorithms. This underscores the ability to the apparatus 10 to monitor and characterize organs' hemodynamic response to changes in blood flow.

Vascular Occlusions

One of the prominent roles of vascular function is its ability to adjust blood flow in response to stimuli. One way of assessing vascular reactivity is by stimulating the vasculature by imposing ischemia on main arteries. To simulate ischemia, we position cuff occlusions upstream of the targeted tissue and then relieve the occlusion after a predetermined period of time.

In this embodiment, we placed a vascular cuff on left arm's brachial artery, and positioned the optical probe on the forearm muscles to record its hemodynamic changes with four wavelengths (680 nm, 780 nm, 800 nm, 820 nm) running at 80 Hz. The cuff inflation with 220 mmHg pressure was started after 20 seconds and was deflated after 30 seconds.

Figure 18A:
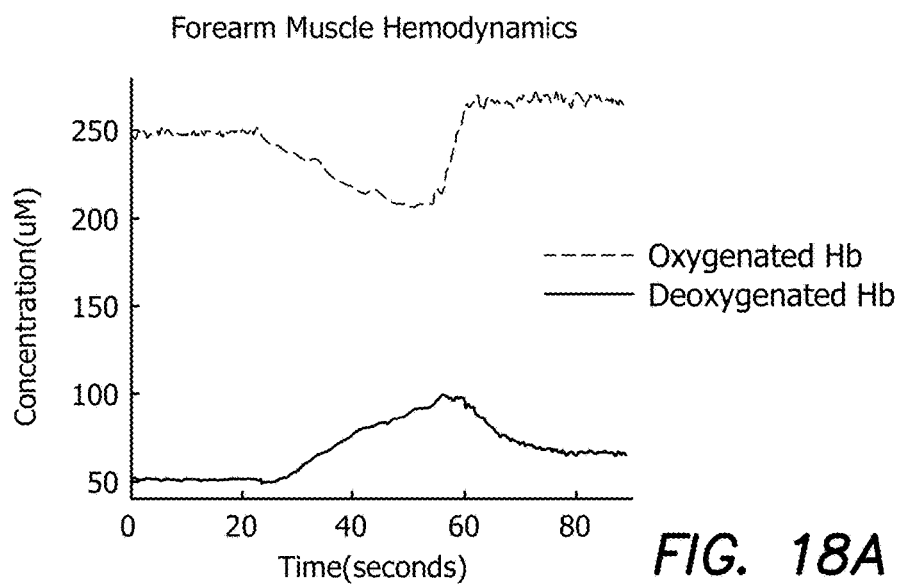
FIG. 18a is time graph of oxy-Hb and deoxy-Hb concentrations in μM occurring in the forearm of a human subject during vascular occlusion as extracted by CWFD.
Figure 18B:
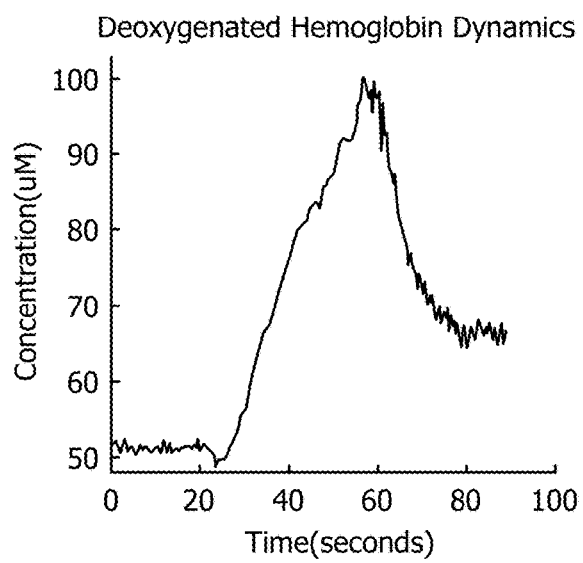
FIGS. 18b and 18c are time graphs of the deoxy-Hb and oxy-Hb dynamics respectively in enlarged scale showing baseline pre-occlusion, ischemia and recovery.
Figure 18C:
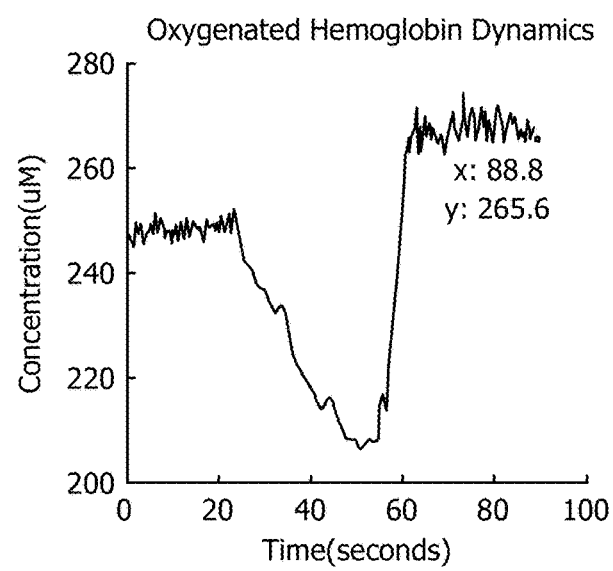

We can split the hemodynamic signal to three phases: a pre-occlusion stage (baseline), an occlusion stage (ischemia), and a post-occlusion stage (recovery). In addition to characterizing vascular reactivity to changes in blood flow, we were able to extract the heart rate from baseline and recovery stages and compare our findings to those from the commercial pulse-oximeter. As a control, we recorded the pulse from the index finger on the same side using a commercial system. We took advantage of the system's fast data acquisition to investigate dynamic changes in blood chromophore concentrations. In FIG. 18a, both oxy- and deoxy-hemoglobin dynamics μM as a function of time are depicted. We also included individual chromophore concentrations to show deoxy-Hb and oxy-Hb dynamics at the baseline and recovery stages shown in FIGS. 18b and 18c respectively.

Figure 19A:
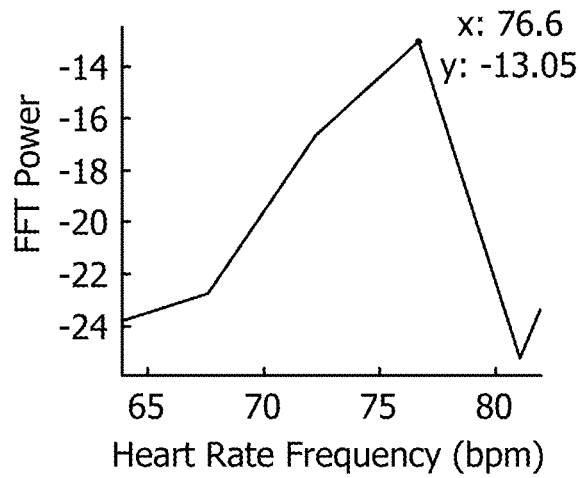
FIG. 19a is the FFT spectrum of a baseline heart rate signal extracted by CWFD from the forearm oxy-Hb of a human subject prior to occlusion as a function of heart rate frequency (bpm).
Figure 19B:
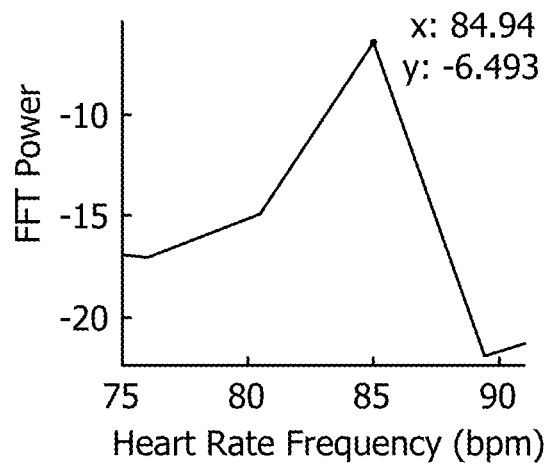
FIG. 19b is the FFT spectrum of a recovery heart rate signal after ischemia as extracted by CWFD from the forearm oxy-Hb as a function of heart rate frequency (bpm).

Again, the same approach (EMD-FFT) as discussed above was used to recover heart rates from oxygenated and deoxygenated hemoglobin throughout the experiment, are shown in FIGS. 19a and 19b. The comparison to the commercial system is summarized in Table 5. We found that after releasing the cuff, heart rate was elevated from baseline values, which might be due to fast reperfusion of blood to the tissue.

TABLE 5

Heart Rate during Vascular cuff occlusion

| Heart Rate (bpm) | Baseline | Recovery |
|---|---|---|
| CW System | 77 | 85 |
| Pulse Oximeter | 71-72 | 80-82 |
| Error | 7.8% | 6.25% |

SUMMARY

Diffuse optical DOSI techniques can provide information about tissue metabolism and architecture non-invasively. Application of this technology includes the characterization and continuous monitoring of hemodynamic changes and vascular reactivity in response to stimuli such as paced breathing and blood flow obstruction. Respiration and heart rates are key physiological parameters that can provide useful information about tissue health. Real time measurement of these physiological parameters with 0.2 to 3 Hz frequency requires an imaging system with high rates of data acquisition (more than 10 Hz). A portable low-cost system helps to lower the barriers to clinical access.

We designed and built a portable high speed continuous-wave tissue functional imaging system 10 that can have various speed from 80-250 Hz based on number of wavelengths needed for the corresponding application. We tested system ability to recover cardio-respiratory signals from thick tissues (muscle and brain) in different settings. We compared part of our findings (heart rate) to those from a commercial system (OHMEDA BIOX 3200) as well. For validating the instrument capability in respiration rate recovery from thick tissues, we instructed the subjects to lock their respiration to a visual metronome (video clip) with 0.25 Hz frequency.

The simplest and most accessible tissue for extracting the vital signals is the fingertip. Monitoring these physiologic parameters provides an important tool for investigation of local tissue metabolism and dysfunction. However recovery of these signals from deep tissues such as muscle and brain are more challenging due to their complex architecture and deeper accessibility. For instance, in the case of the brain, large-source detector separation is needed to penetrate deep and access its vasculature. Our system can measure optical properties in real-time up to a 4 cm source-detector spacing which meets the requirement for brain measurements.

First we were able to replicate pulse-oximeters results by extraction of pulse rate from the fingertip. Next, we recorded optical signals from subjects' brain frontal cortex and wrist muscle. The challenge in obtaining heart rate arises from the fact that non-invasive access to muscle and brain tissue hemoglobin oxygenation requires extracting information through a top layer (e.g., fat or skull) with thickness ranging from a few millimeters to over a centimeter. Therefore, recorded data would be noisier in comparison to those from the fingertip. We used different approaches to analyze the data for the fingertip. In the first approach, we developed peak searching algorithms to find local maximums in optical signals in time domain, and divided their count by duration and multiplied by 60 to get pulse per minute. In the second approach, we applied Fast Fourier Transform algorithms on data to find corresponding peaks of the cardiac cycle in the frequency spectrum. For both approaches, we first removed motion artifacts and noise by using an EMD algorithm. For analyzing muscle and brain measurements, we utilized the second approach, since both methods' results agree with each other for the fingertip. During all measurements, we recorded pulse using commercial system for validating our results. In the worst case (during brain measurements), the recovered heart rates are 6.49% different from conventional commercial system values. As we moved from fingertip to brain measurements, we noticed the error in calculations also increased from 1.35% to 6.49%. The reason for increased inaccuracy in heart rates recovered from muscle and brain tissue is a dramatic decrease in the signal-to-noise ratio and consequently signal quality. Access to these tissue vasculatures requires larger source-detector separations which results in lower signal levels on the detector side. The existence of a cardiac pulse in tissue could be an indicator for presence of localized arterial flow. On the other hand, the absence or abnormal recovered heart rate would be a symptom of tissue malfunction.

In the second embodiment, we used our system to recover a respiration rate which is another important vital signal in clinical settings. Subjects were instructed to synchronize their breath to a 0.25 Hz signal using a video clip. Optical data (four wavelengths) was recorded from wrist and triceps muscle tissue with 2 cm source-detector separation at 80 Hz rate. Combination of EMD-FFT was again utilized to extract desired information. We were able to characterize the vasculature response to the stimuli by extract the induced frequency from both time domain and frequency domain signals of oxygenated and deoxygenated hemoglobin concentrations. In the wrist tissue, time domain result (EMD) showed four peaks during sixteen seconds which corresponds to a 0.25 Hz signal in frequency domain. The respiration rate recovered from oxy-Hb by FFT method was 0.235 Hz while the deoxy-Hb showed a 0.230 Hz peak (2.2% difference). In the arm tissue, measurement duration was increased from sixteen seconds to forty-four seconds. In this case, FFT method recovered a 0.254 Hz peak which is close (8% difference) to the value recovered for deoxy-Hb 0.235 Hz. EMD time domain data showed ten peaks during forty-four seconds instead of eleven. The main reason for this phenomenon is the subject inability to maintain constant 0.25 Hz respiration rate over the period of measurements. The EMD mode used in the wrist tissue was six while in the muscle it was seven. There are different reasons for this phenomena, one can be because of lower SNR in more scattering and absorbing tissue which would results in more noise in the data and more primary modes (high frequency) in EMD. The next reason can be subjects' motions and movements which results in higher modes (low frequency) in EMD. Another reason for performing these measurements and analysis was investigation of tissue ability to adjust its hemodynamics in response to changes induced by paced breathing. In case of tissue vasculature dysfunction, it would be unable to respond to the stimulus. Consequently, the recovered respiration rate would be significantly different from paced breathing frequency.

In a third embodiment, we used the continuous-wave system for characterizing muscle vasculature reactivity to changes in blood flow. Cardiovascular disease impairs the vessels' ability to change their diameter and architecture in response to stimuli. Cuff occlusion is a common method for assessing vasculature reactivity and changing blood flow. We chose the left arm's brachial artery for the occlusion site and forearm muscle for optical monitoring. It has been established to analyze the rate of tissue ischemia and recovery to assess vascular reactivity. In addition to this parameter, we also took advantage of system high speed data acquisition to look at dynamic changes in oxygenated hemoglobin and recover heart rate during the measurements. We compared our pulse rate results to ones from commercial pulse oximeter system since we used it to monitor the index finger. They are in agreement with less than 8% differences. This shows the system ability to monitor hemodynamics changes in response to different stimuli and recover vital signals continuously. After cuff release, we observed an increase in heart rate (85 bpm) in muscle tissue in comparison to the baseline value (77 bpm). This can be caused by sudden release of cuff occlusion and fast reperfusion of blood to the tissue (hyperemia). Characterization and investigation of vasculature response to various modified blood perfusion conditions have significant clinical values. For instance, in the case of diabetic patients with peripheral vascular disease, their tissue hemodynamic response to blood flow blockage and re-perfusion would be significantly different from normal subjects due to their vasculature dysfunction.

What is disclosed is a low cost portable high speed quantitative system for diffuse optical spectroscopic imaging of human tissue. The hybrid system (CWFD) measures absolute optical properties from 660 nm to 980 nm and recovers all tissue chromophore concentrations. The stand-alone FD module can be utilized to measure scattering at every measurement and recover deoxygenated and oxygenated hemoglobin concentrations. The CW module can operate concurrently with the FD module to also measure water and lipid. For applications where scattering changes are negligible, a single FD measurement can be used as a baseline and the CW module can be used for subsequent high-speed measurements to extract the absolute chromophore absorption coefficients.

Finally, if only relative changes in tissue content, (e.g., oxygen saturation) are desired, the instrument can operate in standalone CW mode. The major advantages of the platform include significantly improvement in temporal and spatial information content in addition to dramatic reduction in cost and size compared to the previous technologies.

The CW system includes a custom-designed laser driver, CW detection platform, hardware circuits, filter design, two dimensional tracking module, FDPM module, and software programs developed to interface and integrate different module of the instrument, calibrate the measurements, and recover optical properties. We have characterized and illustrated main parameters of the system, including operation speed, dynamic range, and instrumention.

The performance of new system to extract phantom optical properties and tissue chromophore concentrations has been compared to the previous DOSI technology. The CWFD recovers optical properties in laboratory setting (phantom study) with maximum 5.8% error in comparison to the conventional DOSI system (SSFD) while the maximum error increases to 9.7% for in-vivo measurements (abdomen tissue).

A methodology has been developed for two-dimensional mapping tissue subsurface via integration of a tracking module with the CWFD system. A high density continuous measurement over a region of interest outperforms the conventional method (discrete measurements over a grid pattern) in estimation of tumor shape and contrast.

We have taken the advantage of CWFD system high temporal resolution and large signal-to-noise ratio to explore tissue oximetry applications. We presented measurement of pulsatile waveforms in thick tissues. Finally, we have used vascular occlusion and paced breathing models to measure and analyze tissue hemodynamics response to changes in blood flow. Continuous monitoring of vasculature response to various modified blood perfusion conditions can provide information about local tissue metabolism and physiological state (dysfunction). The low cost, portable, high speed, and quantitative characteristics of this instrument, it is ideal for point-of-care settings.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. An apparatus for combining continuous wave and frequency domain diffuse optical spectroscopic imaging (CWFD DOSI) comprising:
   a frequency domain photon migration (FDPM) module;
   a continuous wave diffuse optical spectroscopic (CW) module; and
   a controller coupled to the FDPM and CW module to control the FDPM module and CW module in a multimode operation which comprises an accuracy derived from a direct measurement of optical scattering from the FDPM module at a speed obtained from the CW module,
   wherein the source of the CW module comprises:
   a laser driver;

an oscillator configured to modulate the laser driver at a frequency of less than 19 KHz to suppress background noise from ambient light on a source and a detector of the CW module; and a narrow bandpass filter coupled to the laser driver, and wherein the detector of the CW module comprises a plurality of narrowband transimpedance amplifiers with active filters disposed after a photodiode configured to detect light from a tissue.

2. The apparatus of claim 1 where the controller in a first mode activates and controls only the FDPM module to make data measurements to provide quantitative data by decoupling scattering from absorption at a plurality of wavelengths sensitive to deoxygenated and oxygenated hemoglobin.

3. The apparatus of claim 1 where the controller in a second mode provides measurements which are quickly obtained but relatively inaccurate by activating activates and controls the CW module at a plurality of data acquisition rates and plurality of wavelengths.

4. The apparatus of claim 1 where the controller in a third mode which provides measurements which are fast and accurate by operating operates the FDPM module once to establish a baseline to measure scattering coefficients for use for later data correction processing and operates operating the CW module to make all remaining measurements.

5. The apparatus of claim 1 where the controller in a fourth mode operates the FDPM module and CW module in an interleaved sequence to take consecutive measurements to measure scattering coefficients for use in later data correction processing in each subsequent measurement.

6. The apparatus of claim 1 further comprising a computer coupled to the controller for processing data measured by the FDPM module and CW module, where the computer calculates quantitative information relating to water, deoxy-Hb, oxy-Hb and lipid in tissue from the data.

7. The apparatus of claim 1 further comprising a probe through which data is obtained by the FDPM module and CW module and a tracking subsystem coupled to the controller to continuously measure linear displacement of the probe and rotational displacement of the probe.

8. The apparatus of claim 1 where the FDPM module and/or CW module include laser sources with wavelengths selected below and above an isosbestic point where both deoxygenated hemoglobin and oxygenated hemoglobin have the same absorption coefficients, so that tissue oximetry is performed.

9. The apparatus of claim 8 further comprising a probe coupled to the FDPM and CW module for data acquisition and where the probe is configured to be applied to thick tissue to measure tissue oxygenation, heart rate, or respiration rate.

10. The apparatus of claim 8 further comprising a probe coupled to the FDPM and CW module for data acquisition and where the probe is configured to be applied to thick tissue to measure tissue oxygenation, heart rate, respiration rate, or dynamic vascular oxygenation response due to vascular occlusion.

11. A method for combining continuous wave and Fourier domain diffuse optical spectroscopic imaging (CWFD DOSI) comprising:

applying an optical probe to thick tissue of a subject;

selectively operating a frequency domain photon migration (FDPM) module coupled to the probe and a continuous wave diffuse optical spectroscopic (CW) module coupled to the probe in a multimode operation, the FDPM and CW modules being operated in combination under control of a computerized controller coupled to the FDPM and CW modules;

continuously tracking a two dimensional position of the probe; and data processing optical scattering and absorption data acquired by the FDPM and CW modules correlated to the continuous tracking of the probe to derive a two dimensional map of a plurality of chromophore concentrations in thick tissue, wherein data processing optical scattering and absorption data acquired by the CW module comprises:

modulating a laser driver within the CW module at a frequency of less than 19 KHz with an oscillator to suppress background noise from ambient light;

filtering an input of the laser driver through a narrow bandpass filter; and filtering detected light from the thick tissue through a plurality of narrowband transimpedance amplifiers with active filters.

12. The method of claim 11 where selectively operating a frequency domain photon migration (FDPM) module coupled to the probe and a continuous wave diffuse optical spectroscopic (CW) module coupled to the probe in a multimode operation comprises in a first mode controlling the FDPM module to make data measurements to provide quantitative data by decoupling scattering from absorption at a plurality of wavelengths sensitive to deoxygenated and oxygenated hemoglobin.

13. The method of claim 11 where selectively operating a frequency domain photon migration (FDPM) module coupled to the probe and a continuous wave diffuse optical spectroscopic (CW) module coupled to the probe in a multimode operation comprises in a second mode controlling the CW module at a plurality of data acquisition rates and plurality of wavelengths.

14. The method of claim 11 where selectively operating a frequency domain photon migration (FDPM) module coupled to the probe and a continuous wave diffuse optical spectroscopic (CW) module coupled to the probe in a multimode operation comprises in a third mode operating the FDPM module once to establish a baseline to measure scattering coefficients for use for later data correction processing and operating the CW module to make all remaining measurements.

15. The method of claim 11 where selectively operating a frequency domain photon migration (FDPM) module coupled to the probe and a continuous wave diffuse optical spectroscopic (CW) module coupled to the probe in a multimode operation comprises in a fourth mode operating the FDPM module and CW module in an interleaved sequence to take consecutive measurements to measure scattering coefficients for use in later data correction processing in each subsequent measurement.

16. The method of claim 11 where data processing optical scattering and absorption data acquired by the FDPM and CW modules correlated to the continuous tracking of the probe to derive a two dimensional map of a plurality of chromophore concentrations in thick tissue comprises calculating quantitative information relating to water, deoxy-Hb, oxy-Hb and lipid in tissue from data acquired by the FDPM and CW modules.

17. The method of claim 11 where continuously tracking a two dimensional position of the probe comprises continuously measuring linear displacement of the probe and rotational displacement of the probe.

18. A method for combining continuous wave and Fourier domain diffuse optical spectroscopic imaging (CWFD DOSI) comprising:

applying an optical probe to thick tissue of a subject;

selectively operating a frequency domain photon migration (FDPM) module coupled to the probe and a continuous wave diffuse optical spectroscopic (CW) module coupled to the probe in a multimode operation which comprises an accuracy derived from a direct measurement of optical scattering from the FDPM module at a speed obtained from the CW module, the FDPM and CW modules being operated in combination under control of a computerized controller coupled to the FDPM and CW modules; and data processing optical scattering and absorption data acquired by the FDPM and CW modules, where the FDPM module and/or CW module include laser sources with wavelengths selected below and above an isosbestic point where both deoxygenated hemoglobin and oxygenated hemoglobin have the same absorption coefficients, so that tissue oximetry is performed, wherein data processing optical scattering and absorption data acquired by the CW module comprises:

modulating the laser source at a frequency of less than 19 KHz with an oscillator to suppress background noise from ambient light;

filtering an input of the laser source through a narrow bandpass filter; and filtering detected light from the thick tissue through a plurality of narrowband transimpedance amplifiers with active filters.

19. The method of claim 18 where data processing to perform tissue oximetry further comprises measuring tissue oxygenation, heart rate, respiration rate, or dynamic vascular oxygenation response due to vascular occlusion.

* * * * *